United States Patent [19]

Kim et al.

[11] Patent Number: 5,593,985

[45] Date of Patent: Jan. 14, 1997

[54] CEPHALOSPORIN COMPOUNDS

[75] Inventors: Joong H. Kim; Sung H. Kim; Ghil S. Nam; Ha Y. Kim; Hyen J. Son; Eun S. Jang, all of Seoul, Rep. of Korea

[73] Assignee: Korea Institute of Science And Technology, Seoul, Rep. of Korea

[21] Appl. No.: 446,353

[22] Filed: May 22, 1995

[30] Foreign Application Priority Data

May 23, 1994 [KR] Rep. of Korea ............ 94-11215
May 18, 1995 [KR] Rep. of Korea ............ 95-12400

[51] Int. Cl.$^6$ .................. C07D 501/46; A61K 31/545
[52] U.S. Cl. .................. 514/203; 540/224; 540/225; 540/216
[58] Field of Search .................. 514/203; 540/224, 540/225, 216

[56] References Cited

U.S. PATENT DOCUMENTS 4,258,041  3/1981  O'Callaghan et al. .............. 544/21

OTHER PUBLICATIONS

Kim et al, Chemical Abstracts, vol. 109, empty 149204 (1988).

Primary Examiner—John M. Ford
Attorney, Agent, or Firm—Anderson Kill & Olick P.C.

[57] ABSTRACT

Novel cephalosporin compounds of formula (I) exhibit potent and broad antibiotic activities against Gram-negative and Gram-positive bacteria and various resistant bacteria:

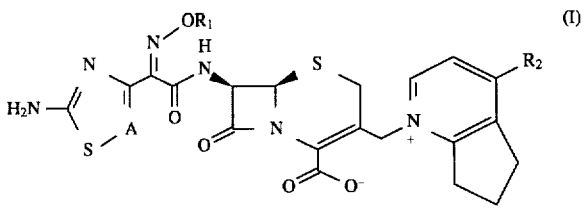

5 Claims, No Drawings

CEPHALOSPORIN COMPOUNDS

FIELD OF THE INVENTION

The present invention relates to novel cephalosporin compounds, hydrates and pharmacologically acceptable salts thereof which possess potent and broad antibacterial activities against Gram-negative and Gram-positive bacteria and various resistant bacteria; and to processes for the preparation thereof.

BACKGROUND OF THE INVENTION

Antibiotics of cephalosporin series are widely used in therapy for the treatment of diseases which are caused by general pathogenic bacteria in human beings and animals. It is known that such antibiotics are useful for the treatment of diseases caused by bacteria-exhibiting resistance to other antibiotics, e.g., penicillin-resistant bacteria; and also for the treatment of penicilin-sensitive patients.

It is also well known that the activity of a cephalosporin compound may be varied by manipulating the substituents on the 3- and/or 7-position of the cephem ring. In this regard, there have been many studies made in developing a variety of cephalosporin antibiotics with broad spectra of antibiotic activities by introducing a 7-β acylamido group and various substituents on the 3-position of the cephem ring.

For example, certain cephalosporin compounds which have the following formula (A) substituted by 2-aminothiazolylacetamino group on the 7-position have been proposed as effective antibiotics against Gram-negative and Gram-positive bacteria:

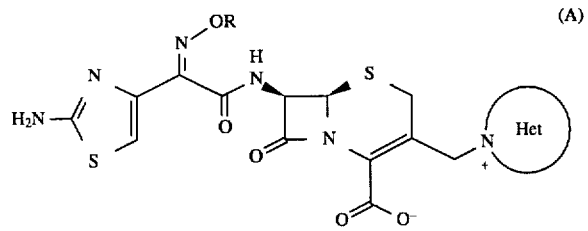

Specifically, cephalosporin compounds of formula (A) having a quaternary aromatic ammonium salt on the 3-position are disclosed in U.S. Pat. No. 4,258,041(ceftazidime), Japanese Laid-Open Patent Publication 86007280(DQ-2556) and EP Application No. 64740(cefpirome). The above cephalosporins are known to exhibit good antibiotic activities against enterobacteria; however, they still suffer from unsatisfactory antibiotic activities against certain bacterial species. For example, ceftazidime has a relatively low activity against Staphylococcus, even though it has a higher activity against Pseudomonas, compared with DQ-2556. Further, cefpirome shows an improved activity against Gram-negative and Gram-positive bacteria, but its activity against Pseudomonas is inferior to ceftazidime.

SUMMARY OF THE INVENTION

Accordingly, it is an object of the present invention to provide novel cephalosporin compounds, hydrates and pharmacologically acceptable salts thereof, which have potent antibiotic activities, especially against Pseudomonas and Staphylococcus species.

Another object of the present invention is to provide processes for the preparation of said cephalosporin compounds.

A further object of the present invention is to provide novel compounds useful as intermediates for the preparation of said cephalosporin compounds.

In accordance with one aspect of the present invention, there is provided a novel cephalosporin compound of formula (I), a hydrate and a pharmacologically acceptable salt thereof,

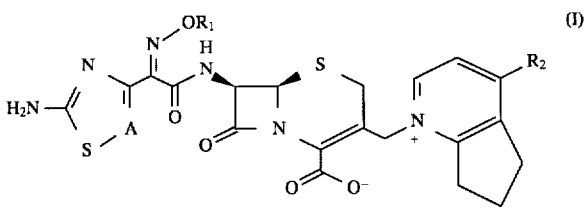

wherein

A is CH or N:

$R_1$ is hydrogen, $C_{1-3}$ alkyl, $C_{1-3}$ halogenated alkyl, $C_{3-5}$ alkenyl, or $C_{2-5}$ carboxyalkyl group: and $R_2$ is an amino group optionally substituted with a formyl, acetyl or methoxycarbonyl group or with one or two $C_{1-3}$ alkyl groups; an aminoalkyl or formylaminoalkyl group; a cyano group;

wherein X is O, S or NOH, and Y is hydroxy, $C_{1-5}$ alkoxy, hydrazino, formylhydrazino, acyl-protected hydrazino, or an amino group optionally substituted with a formyl, $C_{1-3}$ alkylcarbonyl, $C_{1-3}$ alkoxycarbonyl or $C_{1-3}$ alkyl group or with a thiazole ring having an optional carboxyalkyl substituent; or a group represented by formula (VI-1), (VI-2) or (VI-3),

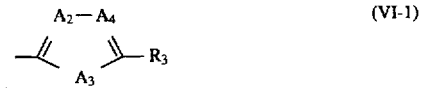

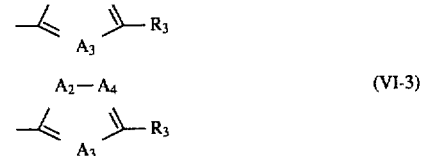

wherein $R_3$ is hydrogen or methyl, $A_2$ is N, O or S, $A_3$ is N or O, and $A_4$ is N, O or CH—.

DETAILED DESCRIPTION OF THE INVENTION

The novel cephalosporin compounds of formula (I) include at least 90)% of syn-isomers ((z)-isomers). The partial structural formulae of 7-position of the syn- and anti-isomers may be represented as:

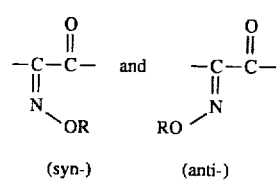

(syn-)     (anti-)

The cephalosporin compound of formula (I) may be prepared by reacting a compound of formula (II) or its salt with a compound of formula (III):

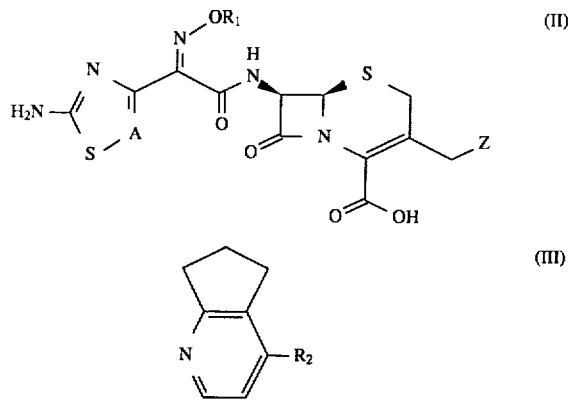

wherein:

A, $R_1$ and $R_2$ have the same meanings as defined previously; and

Z is an acetoxy group or a halogen, preferably iodide or bromine.

In the above reaction, it is preferred to employ the compound of formula (II) wherein Z is acetoxy, or its salt, for example, a sodium or potassium salt. The reaction may be carried out in an aqueous solvent or under an anhydrous condition, i.e., in an organic solvent. The aqueous solvent is preferably water, or an aqueous mixture of an organic solvent which is readily miscible with water, for example, acetone, acetonitrile, dimethylformamide, dioxane, dimethylsulfoxide, ethanol or methanol, or mixtures thereof. The reaction may be carried out at a temperature ranging from 20° to 80° C. and under a neutral condition, preferably under pH 5 to 8. The compound of formula (III) is used in an amount ranging from 1 to 5 molar equivalents based on the compound of formula (II). The reaction may be accelerated by adding 5–20 equivalents of sodium iodide.

Under an anhydrous condition, the reaction may be carried out at a temperature ranging from −30° to 50° C. for 30 minutes to 10 hours. Suitable organic solvents are, for example, nitriles, e.g., acetonitrile, propionitrile, benzonitrile, etc.; halogenated alkyls, e.g., carbon tetrachloride, chloroform, dichloromethane, etc.; ethers, e.g., tetrahydrofuran, dioxane, etc.; amides, e.g., N,N-dimethylformamide; esters, e.g., ethyl acetate, methylacetate, t-buthyl acetate, etc.; ketones, e.g., acetone, methylethyl ketone, methylisobutyl ketone, etc.; aromatic hydrocarbons, e.g., benzene, toluene, etc.; and mixtures thereof.

In order to protect both amine group and carboxyl group and to increase the solubility of the compound of formula (III), a silylization reagent, e.g., N,5-bis(trimethylsilyl)acetamide or N-methyl-N-trimethylsilyl-trifluoroacetamide, may be used.

Most of the formula (III) compounds, which may be employed in the present invention, are novel compounds, except 4-cyano-, 4-carboethoxy-, 4-thiocarbamoyl- and 4-carbamoyl-2,3-cyclopentenopyridine compounds. They may be prepared by employing a known method, for example, the process described in Bull. Soc. Chim. Fr., 687, 692 (1958) or Synthetic Comm., 19(17), 3027 (1989). For example, the novel compound of formula (III) may be prepared from 2,3-cyclopenteno-4-carboethoxypyridine which is obtained by the esterification of 2,3-cyclopenteno-4-carboxypyridine.

The cephalosporin compound of formula (I) may be prepared by reacting 7-aminocephalosporin compound of formula (V) or its acid addition salt with a compound of formula (IV) or its active derivative, and, if necessary, by removing the protecting group:

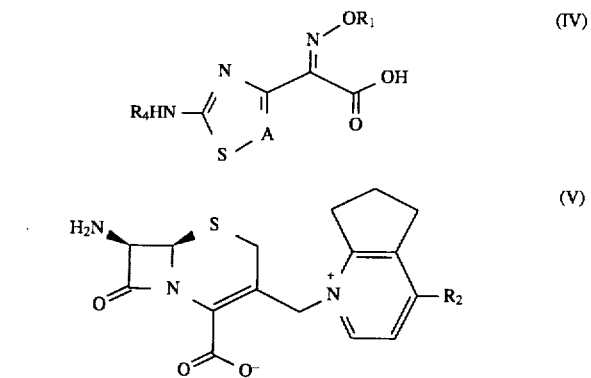

wherein:

A, $R_1$ and $R_2$ have the same meanings as defined previously; and $R_4$ is a hydrogen or amino-protecting group.

In the above reaction, the compound of formula (V) or its acid addition salt formed with an inorganic acid, e.g., hydrochloric acid, hydrobromic acid, nitric acid, hydroiodic acid, phosphoric acid, or an organic acid, e.g., methanesulfonic acid, p-toluenesulfonic acid addition salts, etc. may be used. The acylation of the compound of formula (V) is preferably carried out by using an active derivative of the compound of formula (IV). 2- Amino group of the compound of formula (IV) is preferably protected by, e.g., a formyl, acetyl, chloroacetyl, dichloroacetyl, trichloroacetyl, methoxy carbonyl, ethoxy carbonyl, butoxy carbonyl, benzyloxy carbonyl, triphenylmethyl, 4-methoxy benzyl or diphenylmethyl group. The carboxyl group in the formula (IV) compound may be protected by, e.g., 4-methoxy benzyl, diphenylmethyl, t-amyl, benzyl, p-nitrobenzyl, t-buthyl, 2,2,2-trichloroethyl, pivaloyloxymethyl or methyl group. In order to protect both amino group and carboxyl group and to increase its solubility, a silylization reagent, e.g., N,5-bis(trimethylsilyl)acetamide or N-methyl-N-trimethylsilyl-trifluoroacetamide, may be preferably used. These amino or carboxyl protecting groups may be readily removed by any of the conventional deprotecting methods. In case that an amino-protected compound of formula (IV) is used as the acylating reagent, the reaction may be advantageously carried out in the presence of a condensing agent, e.g., carbodiimide, e.g., N,N'-dicyclohexylcarbodiimide.

Suitable active derivatives of the compound of formula (Iv) include halides, preferably chlorides, which can be obtained by any of the conventional method which are well known in the field of cephalosporin antibiotics, for example, by treating with a halogenating agent, e.g., phosgene, phosphorus pentachloride or thionyl chloride. Other active derivatives of the compound of formula (IV) are anhydrides and mixed anhydrides of, e.g., those formed with lower alkanoic acids, preferably acetic acids, trichloracetic acid, pivalic acid. Particularly preferred active derivatives are those formed with p-nitrophenol, 2,4-dinitrophenol, N-hydroxysuccinimide or N-hydroxyphthalimide, especially 1-hydroxybenzotriazole.

The reaction of the cephem derivatives of formula (V) with carboxylic acids of the formula (IV) may be carried out in the presence of an inert solvent. Suitable solvents include chlorinated hydrocarbons, e.g., methylene chloride or chloroform, ethers, e.g., tetrahydrofuran, dioxane or diethyl ether, ketones, e.g., acetone or methylethylketone, amides, e.g., dimethylformamide or dimethylacetamide, water or mixtures thereof. The reaction may be carried out at a temperature ranging from about −70° to about 80° C., preferably from −30° to 50° C.

The compounds of formula (V) are novel compounds useful as intermediates for preparing the cephalosporin compounds of the present invention. They may be prepared from 7-aminocephalosporanic acid by employing a known method such as those described in JOC, 53, 983(1988).

The separation and purification of the compounds of formula (I) may be carried out by using a conventional method such as recrystallization, column chromatography or ion-exchange chromatography.

The pharmacologically acceptable salts of the compounds of formula (I) can be prepared by stirring the cephalosporin derivatives of the formula (I) at a temperature ranging from 0° to 5° C. for 2 to 8 hours in an aqueous solution of an inorganic or organic acid, preferably an aqueous solution containing 1 to 10 equivalents of an inorganic or organic acid.

The pharmacologically acceptable salts, especially non-toxic salts, of the compounds (I) include salts with a metal, e.g., an alkali metal, e.g., sodium, potassium, etc., or an alkaline earth metal, e.g., calcium, magnesium, etc.; salts with an amine, e.g., trimethylamine, triethylamine, pyridine, procaine, dicyclohexylamine, N-methylglucamine, diethanolamine, triethanolamine, phenylethylbenzylamine, dibenzylethylenediamine, etc.; organic salts with carboxylic or sulfonic acid, e.g., acetate, malate, tartrate, fumarate, citrate, succinate, lactate, oxalate, methanesulfonate, benzenesulfonate, p-toluenate, p-toluenesulfonate,etc.; salts with a basic or acidic amino acid, e.g., arginine, aspartic acid, glutamic acid, lysine, etc.; and salts with an inorganic acid, e.g., hydrochloride, hydrobromide, hydroiodide, phosphate, sulfate, etc.

The compounds of formula (I) and their salts in accordance with the present invention exhibit potent and broad antibiotic activities against a variety of pathogenic microorganisms including Gram-negative and Gram-positive bacteria, especially, against Staphylococcus and Pseudomonas.

The pharmaceutical compositions of the present invention comprise the compounds of formula (I), hydrates or pharmacologically acceptable salts thereof as an active ingredient, and pharmacologically acceptable carriers. In general, it is advantageous to parenterally administer the active compounds of formula (I) in an amount ranging from 50 to 1,500 mg, preferably 100 to 1,000 mg, per day for human adults.

The pharmaceutical compositions of the present invention may be formulated into solid forms such as tablets, capsules or powder, or liquid forms such as injection (intravenous injection, intramuscular injection), suspension or syrup, which may contain conventional additives such as a dispersant, suspending agent, stabilizer and the like.

The following Preparation Examples and Examples are provided for the purpose of illustrating certain aspects of the present invention in more detail; and are not to be construed as limiting the scope of the present invention in any way.

Preparation Example 1

Synthesis of 2,3-cyclopenteno-4-carbamoylpyridine (Formula (III), $R_2$ is

0.50 g (2.62 mmol) of 2,3-cyclopenteno-4-ethoxycarbonyl pyridine was suspended in 10 ml of ammonia water, ammonia gas was introduced thereto at a temperature of 70°±10° C. for 2 hours, and then, the resulting mixture was cooled to 20° C. Aqueous layer was extracted with chloroform (20 ml×3), and the extract was dried over potassium carbonate, filtered, and then evaporated in a rotary evaporator to obtain 0.33 g of the title compound as a gray solid (yield: 78%).

Mass spectrum: m/z=162

M.p.: 202.5° C.

NMR (DMSO-$d_6$): 1.96(quintet, 2H, J=7.8 Hz), 2.93(t, 2H, J=7.8 Hz), 3.03(t, 2H, J=7.8 Hz), 7.41(d, 1H, J=5.5 Hz), 7.67(d, 1H, J=5.5 Hz), 8.00(brs, 1H), 8.53(brs, 1H)

IR(KBr): 3330, 1676 cm$^{-1}$

Preparation Example 2

Synthesis of 4-methoxycarbonyl-2,3-cyclopentenopyridine (Formula (III), $R_2$ is

To a solution of 0.20 g (1.05 mmol) of 2,3-cyclopenteno-4-ethoxycarbonylpyridine in 20 ml of methanol was added 4–5 drops of concentrated hydrochloric acid, and the resulting mixture was stirred at a temperature of 50°–60° C. for 5 hours. The resultant was evaporated in a rotary evaporator to remove the solvent. The residue was extracted with chloroform (20 ml×3), and the extract was dried over potassium carbonate, filtered, and then evaporated in a rotary evaporator to obtain 0.15 g of the title compound as a colorless liquid (yield: 81%).

Mass spectrum: m/z=177

NMR (CDCl$_3$): δ2.13(quintet, 2H, J=7.5 Hz), 3.10(t, 2H, J=7.5 Hz), 3.35(t, 2H, J=7.5 Hz), 4.01(s, 3H), 7.63(d, 1H, J=5.5 Hz), 8.56(d, 1H, J=5.5 Hz)

Preparation Example 3

Synthesis of 2,3-cyclopenteno-4-thiocarbamoylpyridine (Formula (III), $R_2$ is

To a solution of 0.30 g (1.85 mmol) of 2,3-cyclopenteno-4carbamoylpyridine in 10 ml of anhydrous pyridine was added 0.43 g (1.94 mmol) of phosphorous pentasulfide. The resulting solution was heated under reflux for 2 hours and cooled to 20° C., and then 80 ml of water was added slowly thereto. The resulting solution was extracted with chloroform (50 ml), and the extract was evaporated in a rotary evaporator to obtain 0.22 g of the title compound as a yellow solid (yield: 67%).

Mass spectrum: m/z=144 (M$^+$−H$_2$S)

M.p.: 174°–175° C.

NMR (DMSO-d$_6$): δ2.00 (quintet, 2H, J=7.8 Hz), 2.69–3.23(m, 4H), 3.35(t, 2H, J=7.5 Hz), 7.16(d, 1H, J=5.1 Hz), 8.42(d, 1 H, J=5.1 Hz), 9.70(brs, 1H), 10.25(brs,1H)

IR(KBr): 3423, 3298, 1664 cm$^{-1}$

Preparation Example 4

Synthesis of
2,3-cyclopenteno-4-(N-methylcarbamoyl)pyridine
(Formula (III), R$_2$ is

C—NHCH$_3$)

A mixture of 0.3 g (1.57 mmol) of 2,3-cyclopenteno-4-ethoxycarbonylpyridine, 0.32 g (4.71 mmol) of methylamine hydrochloride and 0.19 g (4.71 mmol) of caustic soda was dissolved in 4 ml of mixed solution of tetrahydrofuran and water (1:1 (v/v)). After sealing the container, the solution was stirred for 6 hours while maintaining the outer temperature at 90° C. The resulting solution was cooled to 20° C. and extracted with chloroform (10×3 ml). The extract was evaporated in a rotary evaporator to obtain 0.12 g of the title compound as a light brown solid (yield: 43%).

Mass spectrum: m/z=176

NMR (CDCl$_3$): δ2.10(quintet, 2H, J=7.3 Hz), 3.01(t, 2H, J=7.3 Hz), 3.05(d, 3H, J=6.0 Hz), 3.22(t, 2H, J=7.3 Hz), 6.85(brs, 1H), 7.32(d, 1H, J=5.6 Hz), 8.52(d, 1H, J=5.6 Hz)

Preparation Example 5

Synthesis of
2,3-cyclopenteno-4-aminomethylpyridine (Formula (III), R$_2$ is CH$_2$—NH$_2$)

To 20 ml of dioxane containing 0.30 g (1.68 mmol) of 2,3-cyclopenteno-4-carbamoylpyridine obtained in Preparation Example 1 and 0.32 g (8.42 mmol) of sodium borohydride was added dropwise 0.51 g (8.55 mmol) of acetic acid diluted with 10 ml of dioxane. The reaction solution was heated under reflux for 2 hours and evaporated in a rotary evaporator to remove the solvent. After adding 20 ml of water, the solution was extracted with chloroform (10×3 ml). The extract was dried over potassium carbonate, filtered, and then distilled under reduced pressure. The residue was purified with column chromatography using ethyl acetate as an eluent to obtain 0.11 g of the title compound as a yellow solid (yield: 44%).

Mass spectrum: m/z=148

NMR (CDCl$_3$): δ1.80(brs, 2H), 2.20(quintet, 2H, J=7.5 Hz), 2.71–3.14(m, 2H), 3.30(t, 2H, J=7.5 Hz), 3.96(s, 2H), 7.43(d, 1H, J=6.0 Hz), 8.46(d, 1H, J=6.0 Hz)

Preparation Example 6

Synthesis of
2,3-cyclopenteno-4-formylaminomethylpyridine
(Formula (III), R$_2$ is CH$_2$NHCHO)

0.20 g (1.13 mmol) of 2,3-cyclopenteno-4-aminomethyl pyridine obtained in Preparation Example 5 was dissolved in 10 ml of formic acid. The reaction solution was heated under reflux for 5 hours and evaporated in a rotary evaporator to obtain 0.13 g of the title compound as a light yellow solid (yield: 55%).

NMR (CDCl$_3$): δ2.12(quintet, 2H, J=7.5 Hz), 2.70–3.26(m, 4H), 4.22(d, 2H, J=6.0 Hz), 6.97(d, 1H, J=5.0 Hz), 7.47(br, 1H), 8.28(d, 1H, J=5.0 Hz), 8.32(s, 1H)

Preparation Example 7

Synthesis of
2,3-cyclopenteno-4-hydrazinocarbonylpyridine
(Formula (III), R$_2$ is

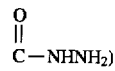
C—NHNH$_2$)

To a solution of 0.30 g (1.57 mmol) of 2,3-cyclopenteno-4-ethoxycarbonylpyridine in 15 ml of ethanol was added 0.78 g (15.67 mmol) of hydrazine monohydrate. The solution was heated under reflux for 5 hours and evaporated under reduced pressure. After adding 20 ml of water, the resultant was extracted with chloroform (10×3 ml) and the extract was evaporated in a rotary evaporator to obtain 0.28 g of the title compound as a light yellow solid (yield: quantitative).

Mass spectrum: m/z=177

NMR (DMSO-d$_6$): δ2.00 (quintet, 2H, J=7.8 Hz), 2.73–3.57(m, 4H), 4.54(brs, 2H), 7.29(d, 1H, J=5.5 Hz), 8.42(d, 1H, J=5.5 Hz), 9.63(brs, 1H)

Preparation Example 8

Synthesis of
2,3-cyclopenteno-4-N-formylhydrazinocarbonyl
pyridine (Formula (III), R$_2$ is

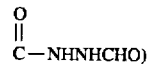
C—NHNHCHO)

0.20 g (1.23 mmol) of 2,3-cyclopenteno-4-hydrazinocarbonylpyridine obtained in Preparation Example 7 was dissolved in 10 ml of formic acid. The solution was heated under reflux for 5 hours and evaporated in a rotary evaporator to obtain 0.23 g of the title compound as a light yellow solid (yield: quantitative).

NMR (DMSO-d$_6$): δ2.02 (quintet, 2H, J=8.0 Hz), 2.96(t, 2H, J=8.0 Hz), 3.07(t, 2H, J=8.0 Hz), 7.27(d, 1H, J=5.2 Hz), 8.07(s, 1H), 8.36(d, 1H, J=5.2 Hz), 9.60(brs, 2H)

Preparation Example 9

Synthesis of
2,3-cyclopenteno-4-(N-(4-carboxymethyl)thiazol-2-yl)aminocarbonylpyridine (Formula (III), R$_2$ is

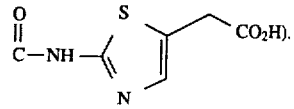

To a mixture of 0.50 g (3.03 mmol) of 2,3-cyclopenteno-4-carboxypyridine and 2.18 ml (30.29 mmol) of thionyl chloride was added 4–5 drops of dimethyl formamide. The resulting mixture was heated under reflux in 20 ml of anhydrous methylene chloride and evaporated in a rotary evaporator to remove the solvent and unreacted thionyl chloride, and then diluted with 20 ml of methylene chloride. To this reaction solution was added 0.89 ml (6.36 mmol) of triethylamine and 0.564 g (3.03 mmol) of ethyl 2-amino-4-thiazoleacetate and the resulting solution was reacted at the temperature of 50° C. for 3 hours and then cooled to 20°–25° C. After adding 20 ml of water, the organic layer was separated, dried over magnesium sulfate, filtered and evaporated under reduced pressure. The obtained residue was suspended in 15 ml of water and 0.1 g of caustic soda was added thereto. The resulting solution was stirred for 10 minutes, and thereto added 1.0N hydrochloric acid solution to adjust pH 6.24. The resulting solution was evaporated in a rotary evaporator and extracted with 20 ml of ethanol to obtain 0.17 g of the title compound as a light brown solid (yield: 19%).

NMR (DMSO-$d_6$): $\delta$1.63–2.30(m, 2H), 2.60–3.56(m, 4H), 3.14(s, 2H), 6.58(brs, 1H), 7.65(d, 1H, J=5.0 Hz), 8.30(brs, 1H)

Preparation Example 10

Synthesis of 2,3-cyclopenteno-4-aminopyridine
(Formula (III), $R_2$ is $NH_2$)

To 25 ml of water was added 1.88 g (46.89 mmol) of NaOH and 0.78 ml (15.06 mmol) of $Br_2$. The resulting solution was added to 25 ml of aqueous suspension of 2.0 g (12.34 mmol) of 2,3-cyclopenteno-4-carbamoylpyridine at 0°–5° C. The reaction solution was heated to 70°–75° C. and cooled to room temperature, and then 10 g of $Na_2S_2O_3$ was added thereto. The resultant was extracted with $CHCl_3$ (50 ml×3), dried over $K_2CO_3$ and evaporated under reduced pressure to obtain 1.40 g of the title compound as a light yellow solid (yield: 85%).

M.p.: 118°–120° C.

NMR (CDCl$_3$): $\delta$1.96(quintet, 2H, J=7.8 Hz), 2.72(t, 2H, J=7.8 Hz), 2.96(t, 2H, J=7.8 Hz), 4.02(brs, 2H, $NH_2$), 6.33(d, 1H, J=5.6 Hz), 8.02(d, 1H, J=5.6 Hz)

IR(KBr): 3472, 3386, 1656, 1605 $cm^{-1}$

Preparation Example 11

Synthesis of
2,3-cyclopenteno-4-acetylaminopyridine (Formula (III), $R_2$ is $NHCOCH_3$)

0.3 g (2.24 mmol) of 2,3-cyclopenteno-4-aminopyridine was dissolved in 5.0 ml of anhydrous acetic acid and the solution was heated at 80°±5° C. for 3 hours. After the reaction was completed, the solution was evaporated under reduced pressure to remove the solvent, washed with 5% $Na_2CO_3$ aqueous solution and dried to obtain 3.6 g of the title compound as a colorless solid (yield: 90%).

NMR (DMSO-$d_6$): $\delta$1.63–2.34(m, 2H), 2.10(s, 3H), 2.60–3.31(m, 4H), 7.71(d, 1H, J=5.5 Hz), 8.34(d, 1H, J=5.5 Hz), 9.42(brs, 1H)

IR(KBr): 3420, 1670 $cm^{-1}$

Preparation Example 12

Synthesis of
2,3-cyclopenteno-4-methoxycarbonylaminopyridine
(Formula (III), $R_2$ is $NHCOOCH_3$)

0.2 g (1.49 mmol) of 2,3-cyclopenteno-4-aminopyridine was diluted with 8.0 ml of $CH_2Cl_2$, and then 0.12 ml (1.57 mmol) of methyl chloroformate diluted with 4.0 ml of $CH_2Cl_2$ was dropped slowly thereto at 0°–5° C. After the reaction was completed, 10 ml of ice water was added to the reaction solution, which was stored at room temperature. 10 ml of 4.0N NaOH was added to the solution, and the resulting solution was extracted with $CH_2Cl_2$ (10 ml×3). The extract was dried over anhydrous $Na_2SO_4$, filtered, evaporated under reduced pressure to obtain 0.15 g of the title compound as a colorless solid (yield: 50%).

M.p.: 192°–193° C.

NMR (CDCl$_3$): $\delta$2.16(quintet, 2H, J=7.2 Hz), 2.84(t, 2H, J=7.2 Hz), 3.06(t, 2H, J=7.2 Hz), 3.84(s, 3H), 6.59(brs, 1H), 7.80(d, 1H, J=5.5 Hz), 8.35(d, 1H, J=5.5 Hz)

IR(KBr): 3380, 1680 $cm^{-1}$

Preparation Example 13

Synthesis of
2,3-cyclopenteno-4-dimethylaminopyridine
(Formula (III), $R_2$ is $N(CH_3)_2$)

To 30 ml of ammonia water was added 0.10 g (4.47 mmol) of sodium, and the solution was stirred at −78° C. for 30 minutes. To the solution, 0.40 g (2.98 mmol) of 2,3-cyclopenteno-4-aminopyridine in 5 ml of dried THF was added slowly at −78° C. The solution was stirred for 1 hour and 0.47 ml (7.45 mmol) of $CH_3I$ diluted with 5 ml of dried THF was added slowly thereto and then heated slowly to room temperature. The resulting solution was evaporated to remove the solvent and subjected to column chromatography over silica gel (230–400 mesh) using methanol and chloroform (1:4, v/v) as an eluent to obtain 0.27 g of the title compound as a light yellow liquid (yield: 56%).

NMR (CDCl$_3$): $\delta$2.10(quintet, 2H, J=7.0 Hz), 2.86(t, 2H, J=7.0 Hz), 3.03(s, 6H), 3.32(t, 2H, J=7.2 Hz), 6.30(d, 1H, J=6.0 Hz), 8.13(d, 1H, J=6.0 Hz)

Preparation Example 14

Synthesis of 2,3-cyclopenteno-4-formaminopyridine
(Formula (III), $R_2$ is NHCHO)

To 6.0 ml of $CH_2Cl_2$ was added 0.50 g (3.73 mmol) of 2,3-cyclopenteno-4-aminopyridine and 0.80 g (3.93 mmol) of dicyclohexylcarbodiimide. To the solution was dropped slowly 1.0 ml of formic acid diluted with 6.0 ml of $CH_2Cl_2$ at 20°±5° C. The resulting solution was stirred for 1 hours and evaporated under reduced pressure to remove the solvent. The residue was subjected to column chromatography over silica gel using as an eluent mixed solution of ethylacetate and n-hexane (4:1, v/v) to obtain 0.24 g of the title compound as a colorless solid (yield: 40%).

m.p.: 188°–189° C.

NMR (DMSO-$d_6$): $\delta$2.34(quintet, 2H, J=7.7 Hz), 3.08(t, 2H, J=7.7 Hz), 3.26(t, 2H, J=7.7 Hz), 8.36(d, 1H, J=5.6 Hz), 8.52(d, 1H, J=5.6 Hz), 8.74(s, 1H), 10.98(s, 1H)

IR(KBr): 3520, 1699 $cm^{-1}$

Preparation Example 15

Synthesis of 2,3-cyclopenteno-4-(4-methylthiazol-2-yl)pyridine (Formula (III), R$_2$ is

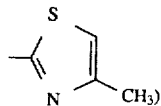

0.20 g (1.10 sol) of 2,3-cyclopenteno-4-thiocarbamoyl pyridine was dissolved in 30 ml of anhydrous ethanol, and 0.21 g (2.27 mmol) of chloroacetone was added thereto and then heated under reflux for 5 hours. To the solution was added 0.21 g (2.27 mmol) of chloroacetone and the resulting solution was heated under reflux for additional 20 hours. After the reaction was completed, the temperature of the reaction solution was lowered to room temperature and the solvent was removed under reduced pressure, and then 20 ml of water was added to the residue. The resulting solution was neutralized with 5% Na$_2$CO$_3$ aqueous solution, extracted with CHCl$_3$ (10 ml×3). The extract was dried over anhydrous Na$_2$SO$_4$, filtered, and evaporated under reduced pressure to obtain 0.14 g of the title compound as a colorless solid (yield: 59%).

M.p.: 69.5°–70° C.

NMR (CDCl$_3$): δ2.16(quintet, 2H, J=7.2 Hz), 2.53(s, 3H), 2.93–3.33(m, 4H), 7.05(s, 1H), 7.66(d, 1H, J=5.0 Hz), 8.59(d, 1H, J=5.0 Hz)

IR(KBr): 2942, 1568cm$^{-1}$

Preparation Example 16

Synthesis of 2,3-cyclopenteno-4-(3-methyl-1,2,4-oxadiazole-5-yl)pyridine (Formula (III), R$_2$ is

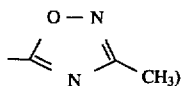

0.20 g (1.23 mmol) of 2,3-cyclopenteno-4-carbamoylpyridine was mixed with 0.48 g (3.60 mmol) of N,N-dimethylacetamido dimethylacetal and the mixture was stirred at 110° C. for 1 hour, and then N,N-dimethylacetamido dimethylacetal was removed therefrom under reduced pressure. To the residue was added 2.5 ml of 1,4-dioxane and 2.5 ml of glacial acetic acid and then added subsequently 0.12 g (1.73 mmol) of hydroxylamine hydrochloride and 0.72 ml of 2M NaOH aqueous solution and the resulting solution was heated under reflux for 2 hours. The solvent was removed under reduced pressure and the residue was dissolved in 30 ml of chloroform. The resultant was washed with water(20 ml×3), dried over anhydrous Na$_2$SO$_4$, filtered, and evaporated under reduced pressure to obtain 0.19 g of the title compound as a colorless solid (yield: 77%).

M.p.: 86°–87.5° C.

NMR (CDCl$_3$): δ2.20(quintet, 2H, J=7.0 Hz), 2.53(s, 3H), 3.03–3.50(m, 4H), 7.73(d, 1H, J=5.0 Hz), 8.59(d, 1H, J=5.0 Hz)

IR(KBr): 2970, 1581 cm$^{-1}$

Preparation Example 17

Synthesis of 2,3-cyclopenteno-4-cyanopyridine (Formula (III), R$_2$ is CN)

0.52 g (2.48 mmol) of anhydrous trifluoric acid was added slowly to a solution of 0.20 g (1.23 mmol) of 2,3-cyclopenteno-4-carbamoylpyridine and 0.25 g (2.47 mmol) of triethylamine dissolved in 5.0 ml of CH$_2$Cl$_2$ at room temperature and stirred for 20 minutes. The solution was washed with water (10 ml×3) and saturated saline (10 ml×3), dried over Na$_2$SO$_4$, filtered, evaporated under reduced pressure to obtain 0.13 g of the title compound as a colorless liquid (yield: 73%).

NMR (CDCl$_3$): δ2.23(quintet, 2H, J=6.6 Hz), 3.10–3.35(m, 4H), 7.32(d, 1H, J=5.0 Hz), 7.59(d, 1H, J=5.0 Hz)

IR(KBr): 2950, 2250 cm$^{-1}$

Preparation Example 18

Synthesis of 2,3-cyclopenteno-4-(N-hydroxycarboxamidyl)pyridine (Formula (III), R$_2$ is

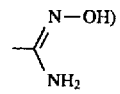

0.13 g (0.90mmol) of 2,3-cyclopenteno-4-cyanopyridine was dissolved in 8 ml of ethanol, and then 0.10 g (1.40 mmol) of hydroxylamine hydrochloride and 0.08 g (1.44 mmol) of KOH were added thereto and heated under reflux for 4.5 hours. After the reaction was completed, the solvent was evaporated under reduced pressure. The residue was washed with water (5 ml), filtered, dried under reduced pressure to obtain 0.033 g of the title compound as a light yellow solid (yield: 20%).

M.p.: 183°–186° C.

NMR (DMSO-d$_6$): δ2.02(quintet, 2H, J=7.2 Hz), 2.90(t, 2H, J=7.2 Hz), 3.06(t, 2H, J=7.2 Hz), 5.84(s, 2H), 7.25(d, 1H, J=5.0 Hz), 8.30(d, 1H, J=5.0 Hz), 9.91(s, 1H)

IR(KBr) : 3447, 3348, 3180, 1654 cm$^{-1}$

Preparation Example 19

Synthesis of 2,3-cyclopenteno-4-(5-methyl-1,2,4-oxadiazol-3-yl)pyridine (Formula (III), R$_2$ is

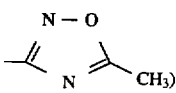

0.072 g (0.54 mmol) of N,N-dimethylacetamide dimethyl acetal was added to 0.033 g (0.18 mmol) of 2,3-cyclopenteno-4-(N-hydroxycarboxamidyl)pyridine and the mixture was stirred at 100° C. for 1 hour. After the reaction was completed, unreacted N,N-dimethylacetamide dimethylacetal was removed under reduced pressure. The residue was subjected to column chromatography over silica gel using as an eluent mixed solution of ethyl acetate and n-hexane (1:2.5, v/v) to obtain 0.029 g of the title compound as an ivory solid (yield: 94%).

M.p.: 87°–88.5° C.

NMR (CDCl$_3$): δ2.17(quintet, 2H, J=6.8 Hz), 2.66(s, 3H), 3.10(t, 2H, J=6.8 Hz), 3.30(t, 2H, J=6.8 Hz), 7.79(d, 1H, J=6.0 Hz), 8.63(d, 1H, J=5.0 Hz)

IR(KBr): 2927, 1599 cm$^{-1}$

Preparation Example 20

Synthesis of 2,3-cyclopenteno-4-(3-methyl-1,2,4-triazol-5-yl)pyridine (Formula (III), R$_2$ is

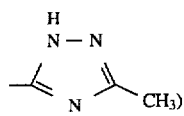

0.20 g (1.23 mmol) of 2,3-cyclopenteno-4-carbamoylpyridine was mixed with 0.48 g (3.60 mmol) of N,N-dimethylacetamido dimethylacetal and the mixture was stirred at 110° C. for 1 hour and then N,N-dimethylacetamido dimethylacetal was removed therefrom under reduced pressure. To the residue was added 1.6 ml of glacial acetic acid and 0.16 g (3.20 mmol) of hydrazine monohydrate and the solution was stirred at 90° C. for 2.5 hours. The reaction solution was cooled to room temperature and 20 ml of water was added thereto. The resultant was neutralized with saturated Na$_2$CO$_3$ aqueous solution, and then extracted with chloroform (30 ml×3). The extract was dried over Na$_2$SO$_4$, filtered, evaporated under reduced pressure to obtain 0.14 g of the title compound as a colorless solid (yield: 58%).

M.p.: 205.5°–208° C. (decomp.)

NMR (CDCl$_3$): δ1.89(quintet, 2H, J=6.8 Hz), 2.30(s, 3H), 2.79(t, 2H, J=6.8 Hz), 3.12(t, 2H, J=6.8 Hz), 7.56(d, 1H, J=4.8 Hz), 8.29(d, 1H, J=4.8 Hz)

IR(KBr): 3042, 2959, 1603 cm$^{-1}$

Preparation Example 21

Synthesis of 2,3-cyclopenteno-4-(1,3,4-oxadiazol-2-yl)pyridine (Formula (III), R$_2$ is

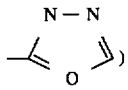

0.21 g (1.19 mmol) of 2,3-cyclopenteno-4-hydrazino carbonylpyridine obtained in Preparation Example 7 was dissolved in 15 ml of ethanol, and 0.30 ml (1.78 mmol) of triethyl orthoformate was added thereto, and then the solution was stirred for 20 hours. After the reaction was completed, the solution was evaporated-under reduced pressure to remove the solvent. The residue was subjected to column chromatography over silica gel using as an eluent mixed solution of CH$_2$Cl$_2$ and methanol (95:5, v/v) to obtain 0.12 g of the title compound as an ivory solid (yield: 54%).

M.p.: 146°–147° C.

NMR (CDCl$_3$): δ2.23(quintet, 2H, J=6.0 Hz), 2.93–3.66(m, 4H), 7.75(d, 1H, J=6.0 Hz), 8.65(d, 1H, J=5.0 Hz), 8.73(s, 1H)

IR(KBr): 2959, 1539 cm$^{-1}$

Preparation Example 22

Synthesis of 7-amino-3-(2,3-cyclopenteno-4-carbamoyl-1-pyridinium)methyl-3-cephem-4-carboxylate hydroiodate 2.72 g (10.0 mmol) of 7-aminocephalosporanic acid was suspended in anhydrous methylene chloride (50 ml) under nitrogen atmosphere, and then 7.0 ml (38.0 mmol) of N-methyl-N-(trimethylsilyl)trifluoroacetamide was added thereto. The reaction solution was heated to the temperature of 40°±5° C. and stirred until it became clear. The resultant was cooled to 20°±5° C. and 4.0 ml (28.0 mmol) of iodotrimethylsilane was added thereto and stirred for additional 30 minutes. To this solution was added 1.91 g (10.0 mmol) of 2,3-cyclopenteno-4-carboethoxypyridine silylized with 3.0 ml (16.0 mmol) of N-methyl-N-(trimethylsilyl)trifluoroacetamide in 10 ml of acetonitrile. The resulting solution was stirred at the temperature of 20°±5° C. for 4 hours, and 50 ml of mixed solution of acetone-methanol (95/5, v/v) was added thereto. After deprotecting, the obtained ivory solid was filtered and dried to give 3.3 g of hydroiodic acid salt as a light yellow solid (yield: 63%).

M.p.: 188° C.$^-$ (decomp.)

NMR (D$_2$O, 300 MHz): δ1.37(t, 3H, J=7.1 Hz), 2.28(quintet, 2H, J=7.3 Hz), 3.15–4.42(m, 8H, SCH$_2$ and cyclopentane, OCH$_2$), 5.05–5.66(m, 4H, NCH$_2$ and 2-lactam), 8.25(d, 1H, J=6.3 Hz), 9.48(d, 1H, J=6.3 Hz)

Preparation Example 23

Synthesis of 7-amino-3-[(2,3-cyclopenteno-4-(N-methylcarbamoyl)-1-pyridinium)methyl]-3-cephem-4-carboxylate hydroiodate The same procedure as described in Preparation Example 22 above was repeated except that 2.72 g (10.0 mmol) of 7-aminocephalosporanic acid and 1.70 g (10.0 mmol) of 2,3-cyclopenteno-4-(N-methylcarbamoyl)pyridine were used as starting materials to obtain 2.8 g of the title compound as an ivory solid (yield: 55%).

M.p.: 191° C. (decomp.)

NMR (D$_2$O, 300 MHz): δ2.63 (quintet, 2H, J=7.3Hz), 2.88 (s, 3H, NHCH$_3$), 3.33–3.48 (m, 6H, SCH$_2$ and cyclopentane), 3.86 (s, 3H), 5.07–5.68 (m, 4H, NCH$_2$ and 2-lactam), 8.16 (d, 1H, J=6.3Hz), 9.43 (d, 1H, J=6.3Hz)

Preparation Example 24

Synthesis of 7-amino-3-(2,3-cyclopenteno-4-carbamoyl-1-pyridinium)methyl-3-cephem-4-carboxylate hydroiodate 2.72 g (10.0 mmol) of 7-aminocephalosporanic acid was suspended in 50 ml of anhydrous methylene chloride under nitrogen atmosphere and 7.0 ml (38.0 mmol) of N-methyl-N-(trimethylsilyl)trifluoroacetamide was added thereto. The solution was heated to the temperature of 40°±5° C. and stirred until it became clear, and then was cooled to 20°±5° C. 4.0 ml (28.0 mmol) of iodotrimethylsilane was added thereto and stirred for additional 30 minutes. To the solution was added 1.62 g (10.0 mmol) of 2,3-cyclopenteno-4-carbamoylpyridine silylized with 3.0 ml (16.0 mmol) of N-methyl-N-(trimethylsilyl)trifluoroacetamide in 10 ml of acetonitrile and stirred at 20°±5° C. for 4 hours. The solution was added to 50 ml of mixed solution of acetone-ethanol (95/5, v/v) to precipitate an ivory solid. The deprotected product was filtered and dried to obtain 3.0 g of the hydroiodic acid salt as a light yellow solid (yield: 59%).

M.p.: 210° C.⁻ (decomp.)

NMR (D$_2$O, 300 MHz): δ2.67(quintet, 2H, J=7.3 Hz), 3.31(t, H,J=7.3 Hz), 3.42(t, 2H, J=7.3 Hz), 3.21, 3.55(ABq, 2H, J$_{gem}$=18.3 Hz), 5.16(d, 1H, J=4.7 Hz), 5.257, 5.42(ABq, 2H, J$_{gem}$=15.0 Hz), 5.86(d, 1H, J=4.7 Hz), 7.93(d, 1H, J=6.5 Hz), 8.71(d, 1H, J=6.5 Hz)

IR(KBr): 1783(β-lactam)

EXAMPLE 1

Synthesis of 7-β-[(Z)-2-aminothiazol-4-yl)-2-methoxyiminoacetamido]-3-[(2,3-cyclopenteno-4-ethoxycarbonyl-1-pyridinium)methyl]3-cephem-4-carboxylate (Formula (I), A is CH, R$_1$ is CH$_3$ and R$_2$ is

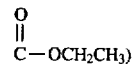

C—OCH$_2$CH$_3$)

(Method a)

0.465 g (1.00 mmol) of Cefotaxime was suspended in 10 ml of anhydrous methylene chloride under nitrogen atmosphere. To this suspension, 0.7 ml (3.8 mmol) of N-methyl-N-(trimethylsilyl)trifluoroacetamide was added and the resulting solution was heated to the temperature of 40°±5° C. and stirred until it became clear. The resulting solution was cooled to 20°±5° C. and 0.4 ml (2.8 mmol) of iodotrimethylsilane was added thereto and stirred for additional 30 minutes. The reaction solution was evaporated in a rotary evaporator to remove the solvent. To the residue was added anhydrous acetonitrile (1.5 ml) and 0.37 ml (4.5 mmol) of tetrahydrofuran, and unreacted iodotrimethylsilane was removed. To this solution was added 0.200 g (1.05 mmol) of 2,3-cyclo-penteno-4-ethoxycarbonylpyridine silylized with 0.3 ml (1.6 mmol) of N-methyl-N-(trimethylsilyl) trifluoroacetamide in 5.0 ml of acetonitrile, and stirred for 4 hours at 20°±5° C. The reaction solution was introduced to 50 ml of mixed solution of acetone-methanol (95/5, v/v) to precipitate an ivory solid. The deprotected product was filtered, dried to obtain iodic salt as a light yellow solid. The obtained salt was dissolved in 2 ml of 5% sodium bicarbonate, subjected to column chromatography over silica gel (230–400 mesh) using as an eluent acetonitrile-water (5:1, v/v) to obtain 0.15 g of the title compound as an ivory solid (yield: 26%).

NMR (DMSO-d6, 300 MHz): δ1.39(t, 3H, J=7.1 Hz) 2.28(quintet, 2H, J=7.3 Hz), 3.16, 3.43(ABq, 2H, J$_{gem}$=17.5 Hz), 3.30(m,4H), 3.80(s,3H), 4.42(q,2H, J=7.1 Hz), 5.05(d, 1H, J=4.7 Hz), 5.31, 5.58(ABq, 2H, J$_{gem}$=14.5 Hz), 5.66(dd, 1H, J=8.0, 4.7 Hz), 6.72(s, 1H), 7.24(brs, 2H), 8.24(d, 1H, J=6.3 Hz), 9.44(d, 1H, J=6.3 Hz), 9.58(d, 1H, J=8.0 Hz)

(Method b)

0.465 g (1.00 mmol) of cefotaxime, 0.092 g (1.10 mmol) of sodium bicarbonate, 2.01 g (12.10 mmol) of potassium iodide and 0.600 g (3.15 mmol) of 2,3-cyclopenteno-4-ethoxycarbonyl pyridine were dissolved in 2.5 ml of water and 0.5 ml of acetonitrile and stirred at 55° C. for 8 hours. This solution was freeze-dried and the residue was subjected to column chromatography over silica-gel (230–400 mesh) using acetonitrile-water (5:1, v/v) as an eluent. The fraction of the product was freeze-dried to obtain 0.15 g of the title compound as a colorless amorphous solid which was the same as obtained in Method a.

EXAMPLE 2

Synthesis of 7-β-[(Z)-2-aminothiazol-4-yl)-2-methoxyiminoacetamido]-3-[(2,3-cyclopenteno-4-carboxy-1-pyridinium)methyl]-3-cephem-4-carboxylate (Formula (I) A is CH, R$_1$ is CH$_3$ and R$_2$ is

C—OH)

0.387 g (0.85 mmmol) of Cefotaxime was suspended in 10 ml of anhydrous methylene chloride under nitrogen atmosphere. The resulting suspension was reacted with 0.7 ml (3.8 mmol) of N-methyl-N-(trimethylsilyl)trifluoroacetamide and 0.4 ml (2.8 mmol) of iodotrimethylsilane, and then concentrated, as described in Example 1 Method a). The resultant was dissolved in 1.5 ml of acetonitrile and 0.37 ml of tetrahydrofuran. To this solution was added 0.14 g (0.86 mmol) of silylized 2,3-cyclopenteno-4-ethoxycarbonylpyridine in 4.0 ml of acetonitrile and reacted for 4 hours. The resulting solution was deprotected as described above to obtain 0.40 g of the hydroiodic acid salt as a light yellow solid. The solid was dissolved in 2 ml of 5% sodium bicarbonate and subjected to column chromatography over silica gel (230–400 mesh) using acetonitrile-water (5:1, v/v) as an eluent to obtain 0.15 g of the title compound as an ivory solid (yield: 32%).

M.p.: 210° C.⁻ (decomp.)

NMR (D$_2$O, 300 MHz): δ2.30(quintet, 2H, J=7.2 Hz), 3.23 (t, 2H, J=7.2 Hz), 3.33(t, 2H, J=7.2 Hz), 3.23, 3.49(ABq, 2H, J$_{gem}$=17.7 Hz), 3.96(s,3H), 5.22(d, 1H, J=4.7 Hz), 5.27, 5.46(ABq, 2H, J$_{gem}$=15.0 Hz), 6.96 (s, 1H), 7.78(d, 1H, J=6.2 Hz), 8.56(d, 1H, J=6.2 Hz)

EXAMPLE 3

A) Synthesis of 7-β-[(Z)-2-aminothiazol-4-yl)-2-methoxyiminoacetamido]-3-[(2,3-cyclopenteno-4-carbamoyl-1-pyridinium)methyl]3-cephem-4-carboxylate (Formula (I), R$_1$ is CH$_3$ and R$_2$ is

C—NH$_2$)

(Method a)

0.465 g (1.00 mmol) of Cefotaxime was suspended in anhydrous methylene chloride (10 ml) under nitrogen atmosphere. The resulting suspension was reacted with 0.7 ml (3.8 mmol) of N-methyl-N-(trimethylsilyl)trifluoroacetamide and 0.4 ml (2.8 mmol) of iodotrimethylsilane, and then concentrated as described in Example 1 (Method a). The resultant was dissolved in 1.5 ml of acetonitrile and 0.37 ml of tetrahydrofuran. To this solution was added 0.14 g (0.86 mmol) of silylized 2,3-cyclopenteno-4-ethoxycarbonylpyridine in 4.0 ml of acetonitrile, and reacted for 4 hours. The reaction solution was deprotected as described above to obtain 0.49 g of hydroiodic acid salt as a light yellow solid. The solid was dissolved in 5% sodium bicarbonate (2 ml), subjected to column chromatography over Silica-gel (230–400 mesh) using acetonitrile-water (5:1, v/v) as an eluent and freeze-dried to obtain 0.28 g of the title compound as an ivory solid (yield: 50%).

M.p.: 170° C.~ (decomp.)

NMR (D$_2$O, 300 MHz): δ2.67(quintet, 2H, J=7.3 Hz), 3.31 (t, 2H,J=7.3 Hz), 3.42(t, 2H, J=7.3 Hz), 3.28, 3.60(ABq, 2H, J$_{gem}$=18.3 Hz), 3.99(s,3H), 5.26(d, 1H, J=4.7 Hz), 5.37, 5.49(ABq, 2H, J$_{gem}$=15.0 Hz), 5.86(d, 1H, J=4.7 Hz), 6.99(s, 1H), 7.93(d, 1H, J=6.5 Hz), 8.71(d, 1H, J=6.5 Hz)

(Method b)

A mixture of 1.00 g (5.00 mmol) of (Z)-2-(2-aminothiazol-4-yl)-2-methoxyiminoacetic acid, 0.76 g (5.00 mmol) of 1-hydroxy-1H-benzotriazole hydrate, 1.14 g (5.50 mmol) of dicyclohexylcarbodiimide and 20 ml of N,N-dimethylformamide was stirred at room temperature for 2 hours. The obtained white solid was filtered and the filtrate was cooled to 0° C. The filtrate was added to mixed solution of 2.5 g (5.00 mmol) of 7-amino-3-(2,3-cyclopenteno-4-carbamoyl-1-pyridinium)methyl-3-cephem-4-carboxylate hydroiodic acid obtained in Preparation Example 24, 10 ml of N,N-dimethylformamide and 1.6 ml (12.70 mmol) of N,N-dimethylaniline. The mixture was stored at room temperature overnight and the precipitate was removed therefrom. The residue was dropped into 500 ml of diethylether with stirring. The precipitate was filtered, triturated with 100 ml of acetone and filtered again. The crude product thus obtained was dissolved in 100 ml of water and insoluble material was discarded by filtration. The resultant was freeze-dried to obtain 1.0 g of the same compound as obtained in Method a (yield: 37%).

B) Synthesis of 7-β-[(Z)-2-(2-aminothiazol-4-yl)-2-methoxy iminoacetamido]-3-((2,3-cyclopenteno-4-carbamoyl-1-pyridinium)methyl]-3-cephem-4-carboxylate tetrahydrates To the solution of 0.3 g of the compound obtained in A) dissolved in 15 ml of water was added 5 ml of acetone, and the resulting solution was stored in refrigerator at 5° C. for 3 days. The crystallized solid was filtered to obtain 0.27 g of the title compound as a monoclinic crystal.

| C$_{23}$H$_{23}$N$_7$O$_6$S$_2$ 4H$_2$O | C | H | N |
|---|---|---|---|
| Theoretical value | 43.87 | 3.68 | 15.57 |
| Experimental value | 43.91 | 3.60 | 15.49 |

The structure of the above crystal was confirmed by X-ray crystallography and the results are shown in Table 1.

TABLE 1

Crystallographic Data of 7-β-[(Z)-2-(2-aminothiazol-4-yl)-2-methoxyiminoacetamido]-3-[(2,3-cyclopenteno-4-carbamoyl-1-pyridinium)methyl]-3-cephem-4-carboxylate tetrahydrates

| | | | |
|---|---|---|---|
| formula | C$_{23}$H$_{23}$N$_7$O$_6$S$_2$.4H$_2$O | F(000) | 660 |
| cryst system | MONOCLINIC | unique data | 1395 |
| space group | P 2$_1$ | no. of reflns | |
| a, Å | 7.007(1) | used, I > 3 σ (I) | 1142 |
| b, Å | 17.684(3) | no. of params | 178 |
| c, Å | 11.292(3) | Z | 2 |
| α, deg | | scan range | 3° < 2θ < 50° |
| β, deg | 98.65(2) | san type | ω-2θ |
| Γ, deg | | μ, cm$^{-1}$ | 0.0703 |
| V, Å | 1383.3(5) | R | 5.60 |
| d$_{calc}$, gcm$^{-3}$ | 1.512 | R$_w$ | 5.75 |
| GOF | 1.17 | Max.inΔρeA$^{3-}$) | 0.31 |

R ]= Σ(|F$_o$| − |F$_c$|)/Σ(|F$_c$|)
R$_w$ = Σ(|F$_o$| − |F$_c$|)$_w$$^{1/2}$/Σ(|F$_c$|)$_w$$^{1/2}$
GOF = [(Σω(|F$_o$| − |F$_c$|/(N$_{data}$ − N$_{params}$)]$^{1/2}$

EXAMPLE 4

Synthesis of 7-β-[(Z)-2-(2-aminothiazol-4-yl)-2-methoxyiminoacetamido]-3-[(2,3-cyclopenteno-4-methoxycarbonyl-1-pyridinium)methyl]-3-cephem-4-carboxylate (Formula (I), A is CH, R$_1$ ia CH$_3$ and R$_2$ is

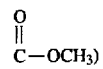

0.410 g (0.90 mmol) of Cefotaxime was suspended in 10 ml of anhydrous methylene chloride under nitrogen atmosphere. The resulting suspension was reacted with 0.7 ml (3.8 mmol) of N-methyl-N-(trimethylsilyl)trifluoroacetamide and 0.4 ml (2.8 mmol) of iodotrimethylsilane, and concentrated as described in Example 1. The resultant was dissolved in 1.5 ml of acetonitrile and 0.37 ml of tetrahydrofuran. To this solution was added 0.160 g (0.90 mmol) of silylized 2,3-cyclopenteno-4-methoxycarbonylpyridine obtained in Preparation Example 2 in 4.0 ml of acetonitrile. The resulting solution was reacted for 4 hours and deprotected to obtain 0.42 g of the hydroiodic acid salt as a light yellow solid. The salt was dissolved in 2 ml of sodium bicarbonate and subjected to column chromatography over silica gel (230–400 mesh) using acetonitrile-water (5:1, v/v) as an eluent and freeze-dried to obtain 0.25 g of the title compound as a light yellow solid (yield: 49%).

M.p.: 173° C.~ (decomp.)

NMR (DMSO-d$_6$, 300 MHz): δ2.28(quintet, 2H, J=7.3 Hz), 3.16, 3.43 (ABq, 2H, J$_{gem}$=17.5 Hz), 3.22–3.42 (m, 4H), 3.80(s, 3H), 5.05(d, 1H, J=4.7 Hz), 5.31, 5.58(ABq, 2H, J$_{gem}$=14.5 Hz), 5.66(dd, 1H, J=8.0, 4.7 Hz), 6.72(s, 1H), 7.24(brs, 2H), 8.24(d, 1H, J=6.3 Hz), 9.44(d, 1H, J=6.3 Hz), 9.58(d, 1H, J=8.0 Hz)

EXAMPLE 5

Synthesis of 7-β-[(Z)-2-(2-aminothiazol-4-yl)-2-methoxyiminoacetamido]-3-[(2,3-cyclopenteno-4-thiocarbamoyl-1-pyridinium)methyl]-3-cephem-4-carboxylate (Formula (I), A is CH, R₁ is CH₃ and R₂ is

2.56 g (5.61 mmol) of Cefotaxime was suspended in 30 ml of anhydrous methylene chloride under nitrogen atmosphere. The resulting suspension was reacted with 1.4 ml (7.6 mmol) of N-methyl-N-(trimethylsilyl)trifluoroacetamide and 0.8 ml (5.6 mmol) of iodotrimethylsilane, and then concentrated as described in Example 1. The resultant was dissolved in 5.0 ml of acetonitrile and 1.04 ml of tetrahydrofuran. To this solution was added 1.00 g (5.61 mmol) of silylized 2,3-cyclo-penteno-4-thiocarbamoylpyridine in 12.0 ml of acetonitrile. The resulting solution was reacted for 6 hours and deprotected to obtain 2.57 g of the hydroiodic acid salt as a light yellow solid. The salt was dissolved in 6 ml of 5% sodium bicarbonate and subjected to column chromatography over silica gel (230–400 mesh) using acetonitrile-water (5:1, v/v) as an eluent, and then freeze-dried to obtain 0.52 g of the title compound as a light yellow solid (yield: 16%).

M.p.: 210° C.⁻ (decomp.)

NMR (DMSO-d₆, 300 MHz): δ2.22(quintet, 2H, J=7.1 Hz), 3.08(t, 2H, J=7.1 Hz), 3.40(t, 2H, J=7.1 Hz), 3.13, 3.42 (ABq, 2H J$_{gem}$=18.8 Hz), 3.80(s, 3H), 5.06(d, 1H, J=4.8 Hz), 5.18, 5.45(ABq, 2H, J$_{gem}$=17.0 Hz), 5.77(dd, 1H, J=8.1, 4.8 Hz), 6.72 (s, 1H), 7.20(brs, 2H), 7.83(d, 1H, J=6.2 Hz), 9.30(d, 1H,J=6.2 Hz), 9.54(d, 1H, J=8.1 Hz), 10.20(brs), 2H)

EXAMPLE 6

Synthesis of 7-β-[(Z)-2-(2-aminothiazol-4-yl)-2-methoxyiminoacetamido]-3-[(2,3-cyclpenteno-4-(N-methylcarbamoyl-1-pyridinium)methyl]-3-cephem-4-carboxylate (Formula (I), A is CH, R₁ is CH₃ and R₂ is

0.45 g (1.00mmol) of Cefotaxime was reacted with 0.4 ml (2.8 mmol) of anhydrous methylsilane and concentrated. The resultant was dissolved in 1.5 ml of acetonitrile and 0.37 ml of tetrahydrofuran. To this solution was added 0.17 g (1.00 mmol) of silylized 2,3-cyclopenteno-4-(N-methylcarbamoyl)pyridine obtained in preparation Example 4 in 4.0 ml of acetonitrile. The resulting solution was reacted for 4 hours and deprotected to obtain 0.54 g of the hydroiodic acid salt as a light yellow solid. The salt was dissolved in 2 ml of 5 sodium bicarbonate and subjected to column chromatography over silica gel (230–400 mesh) using acetonitrile-water (5:1, v/v) as an eluent, and then freeze-dried to obtain 0.21 g of the title compound as a light yellow solid (yield: 37%).

M.p.: 170° C.⁻ (decomp.)

NMR (DMSO-d₆, 300 MHz): δ2.63(quintet, 2H, J=7.3 Hz), 2.88(d, 3H, J=4.0 Hz), 3.33(t, 2H, J=7.3 Hz), 3.19, 3.51(ABq, 2H, 3.86(s, 3H), J$_{gem}$=17.6 Hz), 3.48(t, 2H, J=7.3 Hz), 5.07(d, 1H, J=4.8 Hz), 5.24, 5.61(ABq, 2H, J$_{gem}$=14.1 Hz), 5.68(dd, 1H, J=4.8, 8.1 Hz), 6.71(s, 1H), 7.13(brs, 2H), 8.16(d, 1H, J=6.3 Hz), 9.38(q, 1H, J=4.0 Hz), 9.43(d, 1H, J=6.3 Hz), 9.61(d, 1H, 8.1 Hz)

EXAMPLE 7

Synthesis of 7-β-[(Z)-2-(2-aminothiazol-4-yl)-2-methoxyiminoacetamido]-3-[(2,3-cyclopenteno-4-formylaminomethyl-1-pyridinium)methyl]-3-cephem-4-carboxylate (Formula (I), A is CH, R₁ is CH₃ and R₂ is CH₂—NHCHO)

0.258 g (0.57 mmol) of Cefotaxime was suspended in 10 ml of anhydrous methylene chloride under nitrogen atmosphere. The resulting suspension was reacted with 0.7 ml (3.8 mmol) of N-methyl-N-(trimethylsilyl)trifluoroacetamide and 0.4 ml (2.8 mmol) of iodotrimethylsilane, and then concentrated as described in Example 1. The resultant was dissolved in 1.5 ml of acetonitrile and 0.37 ml of tetrahydrofuran. To this solution was added 0.10 g (0.57 mmol) of silylized 2,3-cyclopenteno-4-formylaminomethylpyridine obtained in Preparation Example 6 in 4.0 ml of acetonitrile. The resulting solution was reacted for 4 hours and deprotected to obtain 0.24 g of the hydroiodic acid salt as a light yellow solid. The salt was dissolved in 2 ml of 5% sodium bicarbonate and subjected to column chromatography over silica gel (230–400 mesh) using acetonitrile-water (5:1, v/v) as an eluent, and then freeze-dried to obtain 0.058 g of the title compound as a light yellow solid (yield: 18%).

M.p.: 179° C.⁻ (decomp.)

NMR (DMSO-d₆, 300 MHz): δ2.28(quintet, 2H, J=7.3 Hz), 3.10(t, 2H, J=7.3 Hz), 3.00–3.50(m, 4H), 3.82(s, 3H), 4.48(d, 2H, J=5.0 Hz), 5.07(d, 1H, J=4.7 Hz), 5.22, 5.48 (ABq, 2H, Jgem=17.0 Hz), 5.67(dd, 1H, J=4.7, 7.9 Hz), 6.71(s, 1H), 7.18(brs, 2H), 7.71(d, 1H, J=6.2 Hz), 8.27(s, 1H), 8.82(t, 1H, J=5.0 Hz), 9.29(d, 1H, J=6.2 Hz), 9.54(d, 1H, J=7.9 Hz)

EXAMPLE 8

Synthesis of 7-β-[(Z)-2-(2-aminothiazol-4-yl)-2-methoxyiminoacetamido]-3-[(2,3-cyclopenteno-4-formylhydrazinocarbonyl-1-pyridinium)methyl]-3-cephem-4-carboxylate (Formula (I), A is CH, R₁ is CH₃ and R₂ is

0.465 g (1.00 mmol) of Cefotaxime was suspended in 10 ml of anhydrous methylene chloride under nitrogen atmosphere. The resulting suspension was reacted with 0.7 ml (3.8 mmol) of N-methyl-N-(trimethylsilyl)trifluoroacetamide and 0.4 ml (2.8 mmol) of iodotrimethylsilane, and then concentrated as described in Example 1. The resultant was dissolved in 1.5 ml of acetonitrile and 0.37 ml of tetrahydrofuran. To this solution was added 0.200 g (0.98 mmol) of silylized 2,3-cyclopenteno-4-formylhydrazinocarbonylpyridine obtained in Preparation Example 9 in 4.0 ml of acetonitrile. The resulting solution was reacted for 4 hours and deprotected to obtain 0.48 g of the hydroiodic acid salt as a light yellow solid. The salt was dissolved in 2 ml of 5% sodium bicarbonate and subjected to column chromatography over silica gel (230–400 mesh) using acetonitrile-water (5:1, v/v) as an eluent, and then freeze-dried to obtain 0.12 g of the title compound as a light yellow solid (yield: 20%).

M.p.: 200° C.⁻ (decomp.)

NMR (DMSO-$d_6$, 300 MHz): δ2.20(quintet, 2H, J=7.2 Hz), 3.01–3.40(m, 6H), 3.85(s, 3H), 5.03(d, 1H, J=4.7 Hz), 5.23, 5.46 (ABq, 2H, Jgem=13.4 Hz), 5.65(dd, 1H, J=4.7, 8.0 Hz), 6.71(s, 1H), 7.20(brs, 2H), 8.01(s, 1H), 8.06(s, 1H), 8.12(s, 1H), 8.30(t, 1H, J=6.7 Hz), 9.22(d, 1H, J=6.7 Hz), 9.55(d, 1H, J=8.0 Hz)

EXAMPLE 9

Synthesis of 7-β-[(Z)-2-(2-aminothiazol-4-yl)-2-methoxyiminoacetamido]-3-[(2,3-cyclopenteno-4-(N-(4-carboxymethylthiazole-2-yl)-aminocarbonyl)-1-pyridinium)methyl]-3-cephem-4-carboxylate (Formula (I), A is CH, $R_1$ is $CH_3$ and $R_2$ is

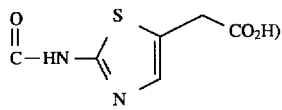

0.210 g (0.46 mmol) of Cefotaxime was suspended in 10 ml of anhydrous methylene chloride under nitrogen atmosphere. The resulting suspension was reacted with 0.4 ml (2.8 mmol) of N-methyl-N-(trimethylsilyl)trifluoroacetamide and 0.4 ml (2.8 mmol) of iodotrimethylsilane, and then concentrated as described in Example 1. The resultant was dissolved in 1.5 ml of acetonitrile and 0.37 ml of tetrahydrofuran. To this solution was added 0.140 g (0.46 mmol) of silylized 2,3-cyclopenteno-4-(N-(4-carboxymethylthiazole-2-yl)-aminocarbonyl)formylhydrazinocarbonylpyridine obtained in Preparation Example 9 in 4.0 ml of acetonitrile. The resulting solution was reacted for 4 hours and deprotected to obtain 0.28 g of the hydroiodic acid salt as a light yellow solid. The salt was dissolved in 2 ml of 5% sodium bicarbonate and subjected to column chromatography over silica gel (230–400 mesh) using acetonitrile-water (5:1, v/v) as an eluent, and then freeze-dried to obtain 0.048 g of the title compound as a light yellow solid (yield: 15%).

M.p.: 210° C.⁻ (decomp.)

NMR (DMSO-$d_6$, 300 MHz): δ2.10(m, 2H), 2.95–3.50(m, 8H), 3.90(s, 3H), 5.20(d, 1H, J=4.7 Hz), 5.30, 5.45(ABq, 2H, $J_{gem}$=15.1 Hz), 5.85(d, 1H, J=4.7 Hz), 6.85(s, 1H), 6.96(s, 1H), 8.00(d, 1H, J=6.6 Hz), 8.73(d, 1H, J=6.6 Hz)

EXAMPLE 10

Synthesis of 7-β-[(Z)-2-(2-aminothiazol-4-yl)-2-carboxyprop-2-oxyimino)acetamido]-3-[(2,3-cyclopenteno-4-carbamoyl-1-pyridinium)methyl]-3-cephem-4-carboxylate Formula (I), A is CH, $R_1$ is $(CH_2)_3COOH$ and $R_2$ is

0.618 g (1.00 mmol) of 7-β-[(Z)-2-(2-aminothiazol-4-yl)-2-carboxyprop-2-oxyimino)acetamido]-3-acetoxymethyl-3-cephem-4-carboxylic acid was suspended in 10 ml of anhydrous methylene chloride under nitrogen atmosphere. The resulting suspension was reacted with 0.4 ml (2.8 mmol) of N-methyl-N-(trimethylsilyl)trifluoroacetamide and 0.4 ml (2.8 mmol) of iodotrimethylsilane, and then concentrated as described in Example 1. The resultant was dissolved in 1.5 ml of acetonitrile and 0.37 ml of tetrahydrofuran. To this solution was added 0.162 g (1.00 mmol) of silylized 2,3-cyclopenteno-4-carbamoylpyridine in 4.0 ml of acetonitrile. The resulting solution was reacted for 4 hours and deprotected to obtain 0.64 g of the hydroiodic acid salt as a light yellow solid. The salt was dissolved in 2 ml of 5% sodium bicarbonate and subjected to column chromatography over silica gel (230–400 mesh) using acetonitrile-water (5:1, v/v) as an eluent, and then freeze-dried to obtain 0.12 g of the title compound as a light yellow solid (yield: 17%).

M.p.: 170° C.⁻ (decomp.)

NMR (DMSO-$d_6$+$D_2O$, 300 MHz): δ1.39(s, 3H), 1.44(s, 3H), 2.22(quintet, 2H, J=7.3 Hz), 3.25(t, 2H, J=7.3 Hz), 3.40(t, 2H,J=7.3 Hz), 3.14, 3.42 (ABq, 2H, $J_{gem}$=17.1 Hz), 5.06(d, 1H, J=5.0 Hz), 5.31, 5.42(ABq, 2H, $J_{gem}$=14.6 Hz), 5.75(d, 1H, J=5.1 Hz), 6.72(s, 1H), 7.92(d, 1H, J=6.2 Hz), 8.98(d, 1H, J=6.2 Hz)

EXAMPLE 11

Synthesis of 7-β-[(Z)-2-(2-aminothiazol-4-yl)-2-methoxyiminoacetamido]-3-[(2,3-cyclopenteno-4-carbamoyl-1-pyridinium)methyl]-3-cephem-4-carboxylate sulfuric acid 0.40 g (0.72 mmol) of 7-β-[(Z)-2-(2-aminothiazol-4-yl)-2-methoxyiminoacetamido]-3-[(2,3-cyclopenteno-4-carbamoyl-1-pyridinium)methyl]-3-cephem-4-carboxylate was dissolved in 4 ml of water and the solution was cooled to 0°–5° C. The resultant was adjusted pH 1–1.5 by adding 3N sulfuric acid and stirred at the same temperature for 1 hour. To this solution was added 10 ml of ethanol and the resulting solution was stirred at the same temperature for 2 hours. The crystalized solid was filtered, washed with ethanol and diethylether, and then dried to obtain 0.41 g of the hydroiodic acid salt as a light yellow solid (yield: 87%).

M.p.: 186° C.⁻ (decomp.)

NMR (DMSO-$d_6$, 300 MHz): δ2.22(quintet, 2H, J=7.3 Hz), 3.24–3.29(m, 4H), 3.40–3.44(m, 2H), 3.82(s, 3H), 5.17(d, 1H, J=4.4 Hz), 5.48, 5.57(ABq, 2H, $J_{gem}$=15.5 Hz), 5.86(td, 1H, J=8.2, 4.4 Hz), 6.73(s, 1H), 7.30(brs, 1H), 8.02(d, 1H, J=6.0 Hz), 8.16(s, 1H), 8.39(s, 1H), 8.76(d, 1H, J=6.0 Hz), 9.65(d, 1H, J=8.2 Hz)

EXAMPLE 12

Synthesis of 7-β-[(Z)-2-(5-amino-1,2,4-thiadiazol-3-yl)-2-methoxyiminoacetamido]-3-[(2,3-cyclopenteno-4-carbamoyl-1-pyridinium)methyl]-3-cephem-4-carboxylate (Formula (I), A is N, $R_1$ is $CH_3$ and $R_2$ is

0.640 g (1.40 mmol) of 7-β-[(Z)-2-(5-amino-1,2,4-thiadiazol-3-yl)-2-methoxyiminoacetamido]-3-acetoxymethyl-3-cephem-4-carboxylic acid was suspended in 10 ml of anhydrous methylene chloride under nitrogen atmosphere. The resulting suspension was reacted with 0.7 ml (3.8 mmol) of N-methyl-N-(trimethylsilyl)trifluoroacetamide and 0.4 ml (2.8 mmol) of iodotrimethylsilane and then concentrated as described in Example 1. The resultant was dissolved in 1.5 ml of acetonitrile and 0.37 ml of tetrahydrofuran. To this solution was added 0.162 g (1.00 mmol) of silylized 2,3-cyclopenteno-4-carbamoylpyridine in 4.0 ml of acetonitrile. The resulting solution was reacted for 4 hours and deprotected as described above to obtain 0.44 g of the hydroiodic acid salt as a light yellow solid. The salt was dissolved in 2 ml of 5% sodium bicarbonate and subjected to column chromatography over silica gel (230–400 mesh) using acetonitrile-water (5:1, v/v) as an eluent, and then freeze-dried to obtain 0.10 g of the title compound as a light yellow solid (yield: 18%).

M.p.: 240° C.⁻ (decomp.)

NMR (DMSO-$d_6$, 300 MHz): $\delta$2.10–2.34(m, 2H), 3.09–3.58(m, 6H), 3.87(s, 3H), 5.02(d, 1H, J=5.1 Hz), 5.20, 5.48(ABq, 2H, $J_{gem}$=14.0 Hz), 5.66(dd, 1H, J=5.1, 8.4 Hz), 7.13(brs, 2H), 8.01(d, 1H, J=6.2 Hz), 8.13(brs, 1H, CON$\underline{H}_a H_b$), 8.43(brs, 1H, CONH$_a\underline{H}_b$), 9.40(d, 1H, J=6.2 Hz), 9.51(d, 1H, J=8.4 Hz)

IR(KBr): 3406, 1774, 1670, 1618, 1396 cm⁻¹

EXAMPLE 13

Synthesis of 7-β-[(Z)-2-(2-aminothiazol-4-yl)-2-ethoxyiminoacetamido]-3-[(2,3-cyclopenteno-4-carbamoyl-1-pyridinium)methyl]-3-cephem-4-carboxylate (Formula (I), A is CH, $R_1$ is $CH_3CH_2$ and $R_2$ is

0.470 g (1.00 mmol) of 7-β-[(Z)-2-(2-aminothiazol-4-yl)-2-ethoxyiminoacetamido]-3-acetoxymethyl-3-cephem-4-carboxylic acid was suspended in 10 ml of anhydrous methylene chloride under nitrogen atmosphere. The resulting suspension was reacted with 0.7 ml (3.8 mmol) of N-methyl-N-(trimethylsilyl)trifluoroacetamide and 0.4 ml (2.8 mmol) of iodotrimethylsilane, and then concentrated as described in Example 1. The resultant was dissolved in 1.5 ml of acetonitrile and 0.37 ml of tetrahydrofuran. To this solution was added 0.162 g (1.00 mmol) of silylized 2,3-cyclopenteno-4-carbamoylpyridine in 4.0 ml of acetonitrile. The resulting solution was reacted for 4 hours and deprotected as described above to obtain 0.37 g of the hydroiodic acid salt as a light yellow solid. The salt was dissolved in 2 ml of 5% sodium bicarbonate and subjected to column chromatography over silica gel (230–400 mesh) using acetonitrile-water (5:1, v/v) as an eluent, and then freeze-dried to obtain 0.10 g of the title compound as a light yellow solid (yield: 18%).

M.p.: 230° C.⁻ (decomp.)

NMR (DMSO-$d_6$, 300 MHz): $\delta$1.17(t, 3H, J=7.2 Hz), 2.69(quintet, H, J=7.3 Hz), 3.35(t,2H, J=7.3 Hz), 3.47(t, 2H, J=7.3 Hz), 3.30, 3.60(ABq, 2H, $J_{gem}$=18.0 Hz), 4.05(q, 2H, J=7.2 Hz), 5.03(d, 1H, J=4.5 Hz), 5.22, 5.46(ABq, 2H, $J_{gem}$=14.0), 5.67(dd, 1H, J=4.5, 7.2 Hz), 6.68(s, 1H), 7.23(brs, 2H), 8.01(d, 1H, J=6.2 Hz), 8.14(brs, 1H, CON$\underline{H}_a H_b$), 8.47(brs, 1H, CONH$_a\underline{H}_b$), 8.71(d, 1H, J=6.5 Hz), 9.34(d, 1H, J=6.2 Hz), 9.54(d, 1H, J=7.2 Hz)

EXAMPLE 14

Synthesis of 7-β-[(Z)-2-(2-aminothiazol-4-yl)-2-(2-fluoroethoxyimino)acetamido]-3-[(2,3-cyclopenteno-4-carbamoyl-1-pyridinium)methyl]-3-cephem-4-carboxylate (Formula (I), A is CH, $R_1$ is $CH_2CH_2F$ and $R_2$ is

The same procedures as described in Example 1 were repeated except that 0.487 g (1.00 mmol) of 7-β-[(Z)-2-(2-aminothiazol-4-yl)-2-(2-fluoroethoxyimino)acetamido]-3-acetoxymethyl-3-cephem-4-carboxylic acid and 0.162 g (1.00 mmol) of 2,3-cyclopenteno-4-carbamoylpyridine were used as starting materials to obtain 0.35 g of hydroiodic acid salt as an light yellow solid. The salt was dissolved in 2 ml of 5% sodium bicarbonate and subjected to column chromatography over silica gel (230–400 mesh) using acetonitrile-water (5:1, v/v) as an eluent, and then freeze-dried to obtain 0.14 g of the title compound as a light yellow solid (yield: 24%).

M.p.: 240° C.⁻ (decomp.)

NMR (DMSO-$d_6$, 300 MHz): $\delta$2.12–2.32(m, 2H), 3.12–3.60(m, 6H), 4.14–4.34(m, 2H, OC$\underline{H}_2$CH$_2$F), 4.49–4.59(m, 2H, OCH$_2$OC$\underline{H}_2$F), 5.04(d, 1H, J=4.5 Hz), 5.23, 5.46(ABq, 2H, $J_{gem}$=14.0 Hz) 5.67(dd, 1H, J=4.5, 8.0 Hz), 6.74(s, 1H), 7.22(brs, 2H), 8.00(d, 1H, J=5.9 Hz), 8.11(brs, 1H, CON$\underline{H}_a H_b$), 8.44(brs, 1H, CONH$_a\underline{H}_b$), 8.71(d, 1H, J=6.5 Hz), 9.33(d, 1H, J=5.9 Hz), 9.59(d, 1H, J=8.0 Hz)

EXAMPLE 15

Synthesis of 7-β-[(Z)-2-(2-aminothiazol-4-yl)-2-(2-propen-1-oxyimino)acetamido]-3-[(2,3-cyclopenteno-4-carbamoyl-1-pyridinium)methyl]-3-cephem-4-carboxylate (Formula (I), A is CH, $R_1$ is CH=CHCH$_2$ and $R_2$ is

The same procedures as described in Example 1 were repeated except that 0.481 g (1.00 mmol) of 7-β-[(Z)-2-(2-aminothiazol-4-yl)-2-(2-propen-1-oxyimino)acetamido]-3-acetoxymethyl-3-cephem-4-carboxylic acid and 0.162 g (1.00 mmol) of 2,3-cyclopenteno-4-carbamoylpyridine were used as starting materials to obtain 0.36 g of hydroiodic acid salt as an light yellow solid. The salt was dissolved in 2 ml of 5% sodium bicarbonate and subjected to column chromatography over silica gel (230–400 mesh) using acetonitrile-water (5:1, v/v) as an eluent, and then freeze-dried to obtain 0.06 g of the title compound as a light yellow solid (yield: 10%).

M.p.: 240° C.⁻ (decomp.)

NMR (DMSO-$d_6$, 300 MHz): $\delta$2.19–2.32(m, 2H, cyclopentane), 3.12–3.71(m, 6H, cyclopentane and SCH$_2$), 4.50–4.63(m, 2H, OC$\underline{H}_2$CH=CH$_2$), 5.03(d, 1H, J=4.8 Hz, $C_6$-lactam-H), 5.10–5.62(m, 4H, OCH$_2$CH=C$\underline{H}_2$, CH$_2$-py), 5.64(dd, 1H, J=4.8, 8.1 Hz, $C_7$-lactam-H), 5.85–6.00(m, 1H, OCH$_2$C$\underline{H}$=CH$_2$), 6.69(s, 1H), 7.23(brs, 2H, NH$_2$), 8.00(d, 1H, J=6.3 Hz), 8.13(brs, 1H, CON$\underline{H}_a$H$_b$), 8.47(brs, 1H, CONH$_a\underline{H}_b$), 9.32(d, 1H, J=6.3 Hz), 9.59(d, 1H, J=8.1 Hz)

EXAMPLE 16

Synthesis of 7-β-[(Z)-2-(2-aminothiazol-4-yl)-2-methoxyiminoacetamido]-3-[(4-amino-2,3-cyclopenteno-1-pyridinium)methyl]-3-cephem-4-carboxylate (Formula (I), A is CH, R$_1$ is CH$_3$ and R$_2$ is NH$_2$)

The same procedures as described in Example 1 were repeated except that 0.465 g (1.00 mmol) of cefotaxime and 0.161 g (1.20 mmol) of 4-amino-2,3-cyclopentenopyridine obtained in Preparation Example 10 were used as starting materials to obtain 0.42 g of hydroiodic acid salt as an light yellow solid. The salt was dissolved in 2 ml of 5% sodium bicarbonate and subjected to HPLC(hypersil column) chromatography using as an eluent acetonitrile-water (1:9, v/v) to obtain 0.12 g of Δ$^3$-isomer and 0.05 g of Δ$^2$-isomer (yield: Δ$^3$ isomer 23%).

M.p.: 180° C.$^-$ (decomp.)

NMR (D$_2$O, 300 MHz): δ2.02(quintet, 2H, J=7.2 Hz, cyclopentane), 2.65(t, 3H, J=7.2 Hz, cyclopentane), 3.00(t, 2H, J=7.2 Hz, cyclopentane), 3.03, 3.35(ABq, 2H, J$_{gem}$=18.5Hz, SCH$_2$) 3.80(s, 3H), 4.90, 4.98(ABq, 2H, J$_{gem}$=15.5Hz, CH$_2$-py), 5.00(d, 1H, J=4.7 Hz, C$_6$-lactam-H), 5.62(d, 1H, J=4.7 Hz, C$_7$-lactam-H), 6.72(s, 1H), 7.40(d, 1H, J=6.5 Hz), 8.35(d, 1H, J=6.5 Hz)

EXAMPLE 17

Synthesis of 7-β-[(Z)-2-(2-aminothiazol-4-yl)-2-methoxyiminoacetamido]-3-[(4-acetamido-2,3-cyclopenteno-1-pyridinium)methyl]-3-cephem-4-carboxylate (Formula (I), A is CH, R$_1$ is CH$_3$ and R$_2$ is NHCOCH$_3$)

The same procedures as described in Example 1 were repeated except that 0.465 g (1.00 mmol) of cefotaxime and 0.211 g (1.20 mmol) of 4-acetamido-2,3-cyclopentenopyridine obtained in Preparation Example 11 were used as starting materials to obtain 0.50 g of hydroiodic acid salt as an light yellow solid. The salt was dissolved in 2 ml of 5% sodium bicarbonate and subjected to column chromatography over silica gel (230–400 mesh) using acetonitrile-water (5:1, v/v) as an eluent, and then freeze-dried to obtain 0.18 g of the title compound as a light yellow solid (yield: 32%).

M.p.: 178° C.$^-$ (decomp.)

NMR (DMSO-d$_6$, 300 MHz): δ2.20(quintet, 2H, J=7.2 Hz, cyclopentane), 2.27(s, 3H), 2.68(t, 2H, J=7.2 Hz, cyclopentane), 3.05(t, 2H, J=7.2 Hz, cyclopentane), 3.10, 3.25(ABq, 2H, J$_{gem}$=18.0 Hz, SCH$_2$), 3.81(s, 3H), 5.01(d, 1H, J=4.5 Hz, C$_6$-lactam-H), 5.15, 5.60(dd, 1H, J$_{gem}$=15.0 Hz, CH$_2$-py), 5.64(q, 1H, C$_7$-lactam-H), 6.71(s, 1H), 7.20(s, 2H), 8.40(d, 1H, J=6.5 Hz), 9.00(d, 1H, J=6.5 Hz), 9.53(d, 1H, J=8.5 Hz, CONH), 10.40(s, 1H, HNCOCH$_3$)

EXAMPLE 18

Synthesis of 7-β-[(Z)-2-(2-aminothiazol-4-yl)-2-methoxyiminoacetamido]-3-[(2,3-cyclopenteno-4-methoxycarnboylamino-1-pyridinium)methyl]-3-cephem-4-carboxylate (Formula (I), A is CH, R$_1$ is CH$_3$ and R$_2$ is NHCOOCH$_3$)

The same procedures as described in Example 1 were repeated except that 0.465 g (1.00 mmmol) of cefotaxime and 0.20 g (1.04 mmol) of 2,3-cyclopenteno-4-methoxycarbonylaminopyridine obtained in Preparation Example 12 were used as starting materials to obtain 0.47 g of hydroiodic acid salt as a light yellow solid. The salt was dissolved in 2 ml of 5% sodium bicarbonate and subjected to column chromatography over silica gel (230–400 mesh) using acetonitrile-water (5:1, v/v) as an eluent, and then freeze-dried to obtain 0.30 g of the title compound as a light yellow solid (yield: 51%).

M.p.: 177° C.$^-$ (decomp.)

NMR (DMSO-d$_6$, 300 MHz): δ2.20(quintet, 2H, J=7.2 Hz, cyclopentane), 2.68(t, 2H, J=7.2 Hz, cyclopentane), 3.05(t, 2H, J=7.2 Hz, cyclopentane), 3.08, 3.38(ABq, 2H, J$_{gem}$=18.5Hz, SCH$_2$) 3.80(s, 3H), 3.82(s, 3H), 5.01(d, 1H, J=4.5 Hz, C$_6$-lactam-H), 5.14, 5.33(dd, 1H, J$_{gem}$=15.5 Hz, CH$_2$-py), 5.62(q, 1H, C$_7$-lactam-H), 6.70(s, 1H), 7.18(s, 2H), 8.25(d, 1H, J=6.5 Hz), 9.00(d, 1H, J=6.5 Hz), 9.54(d, 1H, J=8.5 Hz, CONH), 10.60(s, 1H, HNCOCH$_3$)

EXAMPLE 19

Synthesis of 7-β-[(Z)-2-(2-aminothiazol-4-yl)-2-(2-methoxyiminoacetamido]-3-[(2,3-cyclopenteno-4-formamido-1-pyridinium)methyl]-3-cephem-4-carboxylate (Formula (I), A is CH, R$_1$ is CH$_3$ and R$_2$ is NHCHO)

The same procedures as described in Example 1 were repeated except that 0.316 g (0.68 mmol) of cefotaxime and 0.110 g (0.67 mmol) of 2,3-cyclopenteno-4-formamidopyridine obtained in Preparation Example 14 were used as starting materials to obtain 0.136 g of the title compound as a light yellow solid (yield: 36%).

M.p.: 178° C.$^-$ (decomp.)

NMR (DMSO-d$_6$, 300 MHz): δ2.20(quintet, 2H, J=7.2 Hz, cyclopentane), 2.68(t, 2H, J=7.2 Hz, cyclopentane), 3.05(t, 2H, J=7.2 Hz, cyclopentane), 3.12, 3.40(ABq, 2H, J$_{gem}$=18.5 Hz, SCH$_2$) 3.82(s, 3H), 5.03(d, 1H, J=4.5 Hz, C$_6$-lactam-H), 5.16, 5.33(dd, 2H, J$_{gem}$=15.5 Hz, CH$_2$-py), 5.65(q, 1H, C$_7$-lactam H), 6.70(s, 1H), 7.20(s, 2H), 8.30(brs, 1H), 8.80(brs, 1H), 9.08(d, 1H), 9.58(d, 1H)

EXAMPLE 20

Synthesis of 7β-[(Z)-2-(2-aminothiazol-4-yl)-2-(carboxyprop-2-oxyimino)acetamido]-3-[(2,3-cyclopenteno-4-formamido-1-pyridinium)methyl]-3-cephem-4-carboxylate (Formula (I), A is CH, R$_1$ is (CH$_2$)$_3$COOH and R$_2$ is NHCHO)

The same procedures as described in Example 1 were repeated except that 2.00 g (3.24 mmol) of 7-β-[(Z)-2-(2-aminothiazol-4-yl)-2-(1,1-dimethylcarbomethylimino)acetamido]-3-acetoxymethyl-3-cephem-4-carboxylic acid and 0.53 g (3.24 mmol) of 2,3-cyclopenteno-4-formamidopyridine were used as starting materials to obtain 0.70 g of the title compound as a light yellow solid (yield: 38%).

M.p.: 179° C.$^-$ (decomp.)

NMR (D$_2$O, 300 MHz): δ1.46(s, 3H), 1.48(s, 3H), 2.30(m, 2H), 3.03(m, 2H), 3.30(t, 2H, J=7.3 Hz), 3.20, 3.45(ABq, 2H), 5.06(d, 1H, J=5.0 Hz), 5.18, 5.38(ABq,2H), 5.20(d, 1H), 5.83(d, 1H), 6.86(s, 1H), 8.42(d, 1H), 8.50(brs, 1H)

EXAMPLE 21

Synthesis of 7-β-[(Z)-2-(2-aminothiazol-4-yl)-2-methoxyiminoacetamido]-3-[(2,3-cyclopenteno-4-dimethylamino-1-pyridinium)methyl]-3-cephem-4-carboxylate (Formula (I), A is CH, $R_1$ is $CH_3$ and $R_2$ is $N(CH_3)_2$)

The same procedures as described in Example 1 were repeated except that 0.23 g (0.50 mmmol) of cefotaxime and 0.082 g (0.50 mmol) of 2,3-cyclopenteno-4-dimethylaminopyridine obtained in Preparation Example 13 were used as starting materials to obtain 0.07 g of the title compound ($\Delta^2$ and $\Delta^3$-isomer) as a light yellow solid (yield: $\Delta^3$ isomer 17%).

M.p.: 178° C.⁻ (decomp.)

NMR (DMSO-$d_6$, 300 MHz): δ2.05(quintet, 2H, J=7.2 Hz, cyclopentane), 3.00(t, 2H, J=7.2 Hz, cyclopentane), 3.20(t, 2H, J=7.2 Hz, cyclopentane), 3.22, 3.40(ABq, 2H, $J_{gem}$=18.5Hz, $SCH_2$) 3.30(s, 6H), 3.87(s, 3H), 5.16, 5.30(dd, 2H, $J_{gem}$=15.5 Hz, $CH_2$-py), 5.35(q, 1H, J=4.5 Hz, $C_7$-lactam-H), 5.60(q, 1H, $C_7$-lactam-H), 6.75(s, 1H), 6.80(d, 2H), 7.20(brs, 2H), 8.31(d, 1H), 9.45(d, 1H)

EXAMPLE 22

Synthesis of 7-β-[(Z)-2-(2-aminothiazol-4-yl)-2-hydroxyiminoacetamido]-3-[(2,3-cyclopenteno-4-formamido-1-pyridinium)methyl]-3-cephem-4-carboxylate (Formula (I), A is CH, $R_1$ is H and $R_2$ is NHCHO)

The same procedures as described in Example 1 were repeated except that 0.442 g (1.00 mmmol) of 7-β-[(Z)-2-(2-aminothiazol-4-yl)-2-hydroxyiminoacetamido]-3-acetoxymethyl-3-cephem-4-carboxylic acid and 0.162 g (1.00 mmol) of 2,3-cyclopenteno-4-formamidopyridine were used as starting materials to obtain 0.108 g of the title compound as a light yellow solid (yield: 20%).

M.p.: 177° C.⁻ (decomp.)

NMR (DMSO-$d_6$, 300 MHz): δ2.20(m, 2H), 2.90(m, 2H), 3.05(m, 2H), 3.15, 3.45(ABq, 2H), 5.03(d, 1H, J=5.0 Hz), 5.38, 5.58(ABq,2H), 5.65(q, 1H), 6.60(d, 1H), 7.12(brs, 2H), 8.25(d, 1H), 8.59(brs, 1H), 8.99(d, 1H), 9.45(d, 1H), 11.52(brs, 1H)

EXAMPLE 23

Synthesis of 7-β-[(Z)-2-(2-aminothiazol-4-yl)-2-methoxyiminoacetamido]-3-[(2,3-cyclopenteno-4-cyano-1-pyridinium)methyl]-3-cephem-4-carboxylate (Formula (I), A is CH, $R_1$ is $CH_3$ and $R_2$ is CN)

The same procedures as described in Example 1 were repeated except that 0.426 g (1.00 mmol) of cefotaxime and 0.085 g (0.589 mmol) of 2,3-cyclopenteno-4-cyanopyridine were used as starting materials to obtain 0.0128 g of the title compound as a light yellow solid (yield: 6%).

M.p.: 179° C.⁻ (decomp.)

NMR (DMSO-$d_6$, 300 MHz): δ2.21(m, 2H), 2.96(m, 2H), 3.12(m, 2H), 3.13, 3.50(ABq, 2H), 3.82(s, 3H), 5.06(d, 1H), 5.38, 5.49(ABq, 2H), 5.66(q, 1H), 6.60(d, 1H), 7.12(brs, 2H), 8.35(brs, 1H), 8.99(d, 1H), 9.45(d, 1H)

EXAMPLE 24

Synthesis of 7-β-[(Z)-2-(2-aminothiazol-4-yl)-2-methoxyiminoacetamido]-3-[(2,3-cyclopenteno-4-(N-hydroxycarboxamidyl-1-pyridinium)methyl]-3-cephem-4-carboxylate (Formula (I), A is CH, $R_1$ is $CH_3$ and $R_2$ is

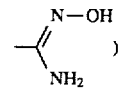

The same procedures as described in Example 1 were repeated except that 0.426 g (1.00 mmol) of cefotaxime and 0.061 g (0.34 mmol) of 2,3-cyclopenteno-4-(N-hydroxycarboxamidyl)pyridine were used as starting materials to obtain 0.029 g of the title compound as a light yellow solid (yield: 15%).

M.p.: 230° C.⁻ (decomp.)

NMR (DMSO-$d_6$, 300 MHz): δ2.20 (m, 2H), 2.96 (m, 2H), 3.10 (m, 2H), 3.10, 3.45(ABq, 2H), 3.83(s, 3H), 5.08(d, 1H), 5.36, 5.49(ABq, 2H), 5.69(q, 1H), 6.80(brs, 1H), 6.85(s, 1H), 7.12(brs, 2H), 7.50(d, 1H), 8.94(d, 1H), 9.45(d, 1H), 10.5(brs, 1H)

EXAMPLE 25

Synthesis of 7-β-[(Z)-2-(2-aminothiazol-4-yl)-2-methoxyiminoacetamido]-3-[(2,3-cyclopenteno-4-(4-methylthiazol-2-yl)-1-pyridinium)methyl]-3-cephem-4-carboxylate (Formula (I), A is CH, $R_1$ is $CH_3$ and $R_2$ is)

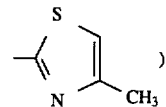

The same procedures as described in Example 1 were repeated except that 0.426 g (1.00 mmol) of cefotaxime and 0.20 g (0.92 mmol) of 2,3-cyclopenteno-4-(methylthiazol-2-yl-pyridine were used as starting materials to obtain 0.25 g of the title compound as a light yellow solid (yield: 44%).

M.p.: 179° C.⁻ (decomp.)

NMR (DMSO-$d_6$, 300 MHz): δ2.30(m, 2H), 2.53(s, 3H), 3.00(m, 2H), 3.10(m, 2H), 3.31, 3.48(ABq, 2H, J=17.7 Hz), 3.82(s, 3H), 5.03(d, 1H, J=17.7 Hz), 5.28, 5.48(ABq, 2H, J=6.2 Hz), 5.65(q, 1H), 6.70(s, 1H), 7.22(brs, 2H), 7.91(s, 1H), 8.40(d, 1H, J=6 Hz), 9.29(d, 1H, J=6 Hz), 9.55(d, 1H, J=7.2 Hz)

EXAMPLE 26

Synthesis of 7-β-[(Z)-2-(2-aminothiazol-4-yl)-2-methoxyiminoacetamido]-3-[(2,3-cyclopenteno-4-(3-methyl-1,2,4-oxadiazol-5-yl)-1-pyridinium)methyl]-3-cephem-4-carboxylate (Formula (I), A is CH, $R_1$ is $CH_3$ and $R_2$ is

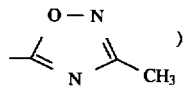

The same procedures as described in Example 1 were repeated except that 0.426 g (1.00 mmol) of cefotaxime and 0.16 g (0.722 mmol) of 2,3-cyclopenteno-4-(3-methyl-1,2,4-oxadiazol-2-yl-pyridine were used as starting materials to obtain 0.05 g of the title compound as a light yellow solid (yield: 11%).

M.p.: 188° C.⁻ (decomp.)

NMR (DMSO-d$_6$, 300 MHz): δ2.28(m, 2H), 2.44(s, 3H), 3.05(m, 2H), 3.14(m, 2H), 3.41, 3.58(ABq, 2H, J=12.8 Hz), 3.86(s, 3H), 5.06(d, 1H, J=4.8 Hz), 5.16, 5.29(ABq, 2H, J=6.0 Hz), 5.65(q, 1H), 6.70(s, 1H), 7.15(brs, 2H), 8.58(d, 1H, J=6 Hz), 9.25(d, 1H, J=6 Hz), 9.54(d, 1H, J=7.2 Hz)

EXAMPLE 27

Synthesis of 7-β-[(Z)-2-(2-aminothiazol-4-yl)-2-methoxyiminoacetamido]-3-[(2,3-cyclopenteno-4-(3-methyl-1,2,4-triazol-5-yl)-1-pyridinium)methyl]-3-cephem-4-carboxylate (Formula (I), A is CH, R$_1$ is CH$_3$ and R$_2$

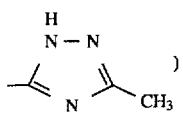

The same procedures as described in Example 1 were repeated except that 0.426 g (1.00 mmol) of cefotaxime and 0.16 g (0.772 mmol) of 2,3-cyclopenteno-4-(3-methyl-1,2,4-triazol-5-yl-pyridine were used as starting materials to obtain 0.211 g of the title compound as a light yellow solid (yield: 45%).

M.p.: 181° C.⁻ (decomp.)

NMR (DMSO-d$_6$, 300 MHz): δ2.20(m, 2H), 2.40(s, 3H), 3.09(m, 2H), 3.18(m, 2H), 3.45, 3.88(ABq, 2H, J=13.8 Hz), 3.85(s, 3H), 5.06(d, 1H, J=4.8 Hz), 5.30, 5.55(ABq, 2H, J=6.0 Hz), 5.70(q, 1H), 6.72(s, 1H), 7.19(brs, 3H), 8.35(d, 1H, J=6.6 Hz), 9.24(d, 1H, J=6.6 Hz), 9.55(d, 1H, J=8.1 Hz)

EXAMPLE 28

Synthesis of 7-β-[(Z)-2-(2-aminothiazol-4-yl)-2-methoxyiminoacetamido]-3-[(2,3-cyclopenteno-4-(1,3,4-oxadiazol-2-yl)-1-pyridinium)methyl]-3-cephem-4-carboxylate (Formula (I), A is CH, R$_1$ is CH$_3$ and R$_2$ is

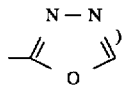

The same procedures as described in Example 1 were repeated except that 0.426 g (1.00 mmol) of cefotaxime and 0.165 g (0.88mmol) of 2,3-cyclopenteno-4-(1,3,4-oxadiazol-2-yl-pyridine were used as starting materials to obtain 0.18 g of the title compound as a light yellow solid (yield: 35%).

M.p.: 183° C.⁻ (decomp.)

NMR (DMSO-d$_6$, 300 MHz): δ2.29(m, 2H), 3.19(m, 2H), 3.20(m, 2H), 3.65, 3.90(ABq, 2H), 3.90(s, 3H), 5.08(d, 1H, J=4.2 Hz), 5.38, 5.68(ABq, 2H, J=6.4 Hz), 5.75(q, 1H), 6.71(s, 1H), 7.20(brs, 3H), 8.45(d, 1H, J=6.2 Hz), 9.48(d, 1H, J=6.2 Hz), 9.58(brs, 2H, CONH, oxadiazole-H)

EXAMPLE 29

Synthesis of 7-β-[(Z)-2-(2-aminothiazol-4-yl)-2-methoxyiminoacetamido]-3-[(2,3-cyclopenteno-4-(3-methyl-1,2,4-oxadiazol-3-yl)-1-pyridinium)methyl]-3-cephem-4-carboxylate (Formula (I), A is CH, R$_1$ is CH$_3$ and R$_2$ is

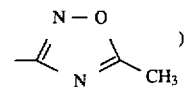

The same procedures as described in Example 1 were repeated except that 0.426 g (1.00 mmol) of cefotaxime and 0.16 g (0.772 mmol) of 2,3-cyclopenteno-4-(5-methyl-1,2,4-oxadiazol-3-yl-pyridine were used as starting materials to obtain 0.10 g of the title compound as a light yellow solid (yield: 22%).

M.p.: 188° C.⁻ (decomp.)

NMR (DMSO-d$_6$, 300 MHz): δ2.29(m, 2H), 2.46(s, 3H), 3.05(m, 2H), 3.14(m,2H), 3.45, 3.56(ABq, 2H, J=14.4 Hz), 3.85(s, 3H), 5.06(d, 1H, J=4.5 Hz), 5.18, 5.24(ABq, 2H, J=6.6 Hz), 5.65(q, 1H), 6.72(s, 1H), 7.15(brs, 2H), 8.55(d, 1H, J=6.6 Hz), 9.25(d, 1H, J=6.6 Hz), 9.54(d, 1H, J=7.2 Hz)

Activity Test

In order to illustrate antibiotic effectiveness of the compounds of the present invention, the minimal inhibitory concentrations (MIC's) of the representative compounds were determined against standard strains and compared with ceftazidime and cefpirome, which were used as control compounds.

The MIC values were taken by employing a two-fold dilution method: that is, two-fold serial dilutions of each of the test compounds were made from initial concentration of 1,000 mg/ml; each 1.5 ml of them was dispersed in 13.5 ml of Muller Hinton agar medium to adjust to 100–0.02 mg/ml; the standard test strain which had the concentration of 10$^7$ CFU/ml was inoculated by medium;and these were incubated at 37° C. for 18 hours.

The test used twenty kinds of standard test strains which induced urinary tract infections, respiratory organ infections, skin soft tissue infections, plasma infections, gastrointestinal infections, central nervous system infections, most of which produce β-lactamase. The standard test strains used are as follows:

Gram-positive bacteria

1. *Streptococcus pyogenes* A 308
2. *Streptococcus pyogenes* A 77
3. *Streptococcus faecium* 8b
4. *Staphylococcus aureus* SG 511
5. *Staphylococcus aureus* 285
6. *Staphylococcus aureus* 503

Gram-negative bacteria

7. *Escherichia coli* 0 55
8. *Escherichia coli* DC 0
9. *Escherichia coli* DC 2
10. *Escherichia coli* TEM
11. *Escherichia coli* 1507 E
12. *Pseudomonas aeruginosa* 9.027
13. *Pseudomonas aeruginosa* 1592 E
14. *Pseudomonas aeruginosa* 1771

15. *Pseudomonas aeruginosa* 1771M
16. *Salmonella typhimurium*
17. *Klebsiella oxytoca* 1082 E
18. *Klebsiella aerogenes* 1552 E
19. *Enterobacter cloacae* P 99
20. *Enterobacter cloacae* 1321 E The results of the MIC tests against the above described standard test strains are given in Table 2. The MIC values of 345 strains clinically separated are shown in Table 3.

As can be seen from the above results, the cephalosporin compounds of the present invention generally exhibit excellent antibiotic activities against Gram-positive and Gram-negative bacteria as compared with the known cephalosporin compounds. Especially, the compounds of Examples 3 and 5 exhibit unexpectedly potent antibiotic activities against MRSA(Yonsei Univ.) which shows resistance to cefpirome.

TABLE 2

Minimal Inhibitory Concentration(MIC) mg/ml

| test strains | Example 1 | 2 | 3 | 5 | 13 | 14 | 17 | 19 | 25 | CTZ | cefpirome |
|---|---|---|---|---|---|---|---|---|---|---|---|
| 1 | 0.007 | 0.025 | 0.0007 | 0.004 | 0.013 | 0.013 | <0.002 | <0.002 | 0.004 | 0.098 | 0.004 |
| 2 | 0.007 | 0.007 | 0.002 | 0.002 | 0.004 | 0.013 | <0.002 | <0.002 | 0.002 | 0.049 | 0.098 |
| 3 | 25 | 25 | 12.5 | 12.5 | 50 | 25 | 100 | 25.0 | 12.5 | 100 | 25 |
| 4 | 1.563 | 6.250 | 0.391 | 0.781 | 0.781 | 0.781 | 0.781 | 0.391 | 0.391 | 12.5 | 0.391 |
| 5 | 3.125 | 6.250 | 0.781 | 1.563 | 3.125 | 1.563 | 0.391 | 0.781 | 12.5 | 0.781 |  |
| 6 | 0.781 | 3.125 | 0.391 | 0.391 | 0.391 | 0.781 | 0.195 | 0.098 | 0.195 | 0.098 | 0.013 |
| 7 | 0.049 | 0.025 | 0.031 | 0.049 | 0.025 | 0.013 | 0.025 | 0.007 | 0.195 | 0.098 | 0.013 |
| 8 | 0.049 | 0.049 | 0.025 | 0.098 | 0.098 | 0.049 | 0.013 | 0.013 | 0.025 | 0.098 | 0.049 |
| 9 | 0.025 | 0.049 | 0.025 | 0.025 | 0.049 | 0.049 | 0.013 | 0.013 | 0.025 | 0.098 | 0.049 |
| 10 | 0.391 | 0.781 | 0.049 | 0.098 | 0.195 | 0.098 | 0.025 | 0.049 | 0.391 | 0.195 | 0.049 |
| 11 | 0.049 | 0.025 | 0.025 | 0.098 | 0.098 | 0.049 | 0.025 | 0.098 | 0.781 | 0.195 | 0.075 |
| 12 | 12.5 | 12.5 | 1.563 | 6.250 | 6.25 | 6.25 | 12.5 | 12.5 | 100 | 3.125 | 3.125 |
| 13 | 12.5 | 12.5 | 1.563 | 3.125 | 3.125 | 6.25 | 6.25 | 12.5 | 50 | 0.781 | 1.563 |
| 14 | 6.250 | 3.125 | 0.391 | 1.563 | 1.563 | 0.781 | 6.25 | 12.5 | 50 | 0.391 | 0.391 |
| 15 | 0.391 | 0.391 | 0.195 | 0.391 | 0.195 | 0.391 | 1.563 | 1.563 | 1.563 | 0.098 | 0.195 |
| 16 | 0.049 | 0.049 | 0.025 | 0.049 | 0.049 | 0.049 | 0.049 | 0.195 | 0.391 | 0.195 | 0.025 |
| 17 | 6.250 | 25 | 1.563 | 3.125 | 3.125 | 3.125 | 6.25 | 1.563 | 3.125 | 0.781 | 3.125 |
| 18 | 0.049 | 0.025 | 0.025 | 0.049 | 0.049 | 0.049 | 0.013 | 0.049 | 0.781 | 0.098 | 0.025 |
| 19 | 25 | 100 | 3.125 | 6.250 | 12.5 | 12.5 | 12.5 | 12.5 | 25 | 100 | 3.125 |
| 20 | 0.025 | 0.025 | 0.007 | 0.013 | 0.025 | 0.025 | 0.013 | 0.007 | 0.098 | 0.025 | 0.013 |

TABLE 3

Minimal Inhibitory Concentration(MIC) with respect to clinically separated strains mg/ml

| microorganisms(no. of test strains) | cepirome range of MIC | MIC 50 | MIC 90 | compound of Example 3 range of MIC | MIC 50 | MIC 90 |
|---|---|---|---|---|---|---|
| *Enterobactercloacas*(20) | 0.013–1.563 | 0.025 | 0.098 | 0.013–1.563 | 0.025 | 0.049 |
| *Escherichia coli*(20) | 0.025–0.391 | 0.025 | 0.049 | 0.025–0.391 | 0.025 | 0.049 |
| Serratia spp(20) | 0.025–0.049 | 0.049 | 0.098 | 0.025–0.049 | 0.025 | 0.049 |
| D *Streptococcus* I(20) | 12.500–100.000 | 25.0 | 50.0 | 12.500–100.000 | 12.5 | 25.0 |
| D *Streptococcus*II(19) | 6.250–100.000 | 50.000 | 100.000 | 6.250–100.000 | 25.000 | 100.000 |
| *Pseudomonas aeruginosa*(20) | 0.781–12.500 | 3.125 | 12.500 | 0.781–12.500 | 3.125 | 6.250 |
| *Pseudomonas* I(19) | 0.781–12.500 | 1.563 | 6.250 | 0.781–12.500 | 3.125 | 6.250 |
| *Pseudomonas* II(19) | 0.781–12.500 | 1.563 | 6.250 | 0.781–12.500 | 1.563 | 6.250 |
| *Streptococcus* I(20) | 0.007–25.000 | 0.025 | 12.500 | 0.007–25.000 | 0.025 | 12.500 |
| *Streptococcus* II(17) | 0.002–0.007 | 0.004 | 0.007 | 0.002–0.007 | 0.004 | 0.007 |
| *Enterococcus* I(20) | 0.013–0.195 | 0.025 | 0.098 | 0.013–0.195 | 0.025 | 0.049 |
| *Enterococcus* II(20) | 0.007–3.125 | 0.049 | 1.563 | 0.007–3.125 | 0.025 | 1.563 |
| *Morganella morganii*(5) | 0.013–0.025 | 0.013 | 0.025 | 0.013–0.025 | 0.013 | 0.025 |
| *Providencia rettgeri*(6) | 0.004–0.098 | 0.049 | 0.013 | 0.004–0.098 | 0.013 | 0.049 |
| *Proteus mirabilis*(4) | 0.007–0.049 | 0.013 | 0.049 | 0.007–0.049 | 0.013 | 0.049 |
| *Proteus vulgaris*(5) | 0.025–0.098 | 0.049 | 0.098 | 0.025–0.098 | 0.025 | 0.098 |
| *Klebsiella oxytoca*(20) | 0.007–0.391 | 0.025 | 0.781 | 0.007–0.391 | 0.013 | 0.098 |
| Methicillin Resistant(19) | 0.781–100.000 | 12.500 | 100.000 | 0.781–100.000 | 6.250 | 50.000 |
| MRSA(KAIST) (15) | 0.781–100.000 | 12.500 | 100.000 | 0.781–100.000 | 6.250 | 50.000 |
| MRSA(Yonsei Univ.) (17) | 100.000–100.000 | 100 | 100.000 | 0.013–100.000 | 12.5 | 100.000 |
| ATCC(20) | 0.013–100.000 | 0.098 | 25.000 | 0.013–100.000 | 0.098 | 25.000 |

In order to illustrate clinical effectiveness of the compounds of the present invention more specifically, the stability to β-lactamase and antibiotic activity against systemic infection, were tested, and the results are shown in Table 4 and 5, respectively.

In the test, β-lactamase separated from *Enterobacter cloacae* P77 was used and cefalolidine was used as a reference compound for comparison.

TABLE 4

| | Relative Hydrolysis (unit: %) | |
|---|---|---|
| antibiotics(100 μM) β-lactamase | cefalolidine | compound of Ex. 3 |
| *Enterobacter cloacae* P77 | 100 | 0.0 |

Antibiotic activity against systematic infection was tested by using mice: that is, 0.3 ml of a strain solution containing fatal dose of bacteria in 0.3 ml was administered to mice intraperitoneally; and then, the test antibiotics were administered intramuscularly in an amount of 5 to 0.078 mg/kg. $PD_{50}$ was calculated by probit method.

TABLE 5

| Antibiotic Activities against Systemic Infection | | |
|---|---|---|
| test strains | administration method | $PD_{50}$ (mg/kg) (confidence limit) compound of Ex. 3 |
| *Streptococcus pyogens* A77 | intramuscular injection | 0.29 (0.19–0.43) |

Acute toxicity test of the compounds of Examples 3 and 5 shows that $LD_{50}$ of each compound of the present invention is generally higher than 3000 mg/kg in case of intravenous injection.

While the invention has been described with respect to the above specific embodiments, it should be recognized that various modifications and changes may be made and also fall within the scope of the invention as defined by the claims that follow.

What is claimed is:

1. A cephalosporin compound of the formula (I), a hydrate and a pharmacologically acceptable salt thereof,

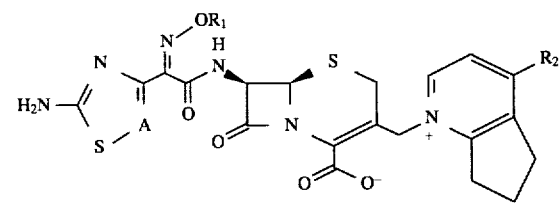

wherein

A is CH or N:

$R_1$ is hydrogen, $C_{1-3}$ alkyl, $C_{1-3}$ halogenated alkyl, $C_{3-5}$ alkenyl, or $C_{2-5}$ carboxyalkyl group: and $R_2$ is an amino group optionally substituted with a formyl, acetyl or methoxycarbonyl group or with one or two $C_{1-3}$ alkyl groups; an aminoalkyl or formylaminoalkyl group; a cyano group;

wherein X is O, S or NOH, and Y is hydroxy, $C_{1-5}$ alkoxy, hydrazino, formylhydrazino, acyl-protected hydrazino, or an amino group optionally substituted with a formyl, $C_{1-3}$ alkylcarbonyl, $C_{1-3}$ alkoxycarbonyl or $C_{1-3}$ alkyl group or with a thiazole ring having an optional carboxyalkyl substituent; or a group represented by formula (VI-1), (VI-2) or (VI-3),

wherein $R_3$ is hydrogen or methyl, $A_2$ is N, O or S, $A_3$ is N or O, and $A_4$ is N, O or CH.

2. The compound of claim 1 which is selected from the group consisting of:

7-β-[(Z)-2-(2-aminothiazol-4-yl)-2-methoxyiminoacetamido]-3-[(2,3-cyclopenteno-4-ethoxycarbonyl-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-carboxy-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-carbamoyl-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-methoxycarbonyl-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-thiocarbamoyl-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-(N-methylcarbamoyl-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-formylaminomethyl-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-formylhydrazinocarbonyl-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-(N-(4-carboxymethylthiazol-2-yl)aminocarbonyl)-1-pyridinium)methyl]-3-cephem-4-carboxylate;

7-β-[(Z)-2-(2-aminothiazol-4-yl)-2-(carboxyprop-2-oxyiminoacetamido]-3-[(2,3-cyclopenteno-4-carbamoyl-1-pyridinium)methyl]-3-cephem-4-carboxylate;

7-β-(Z)-[2-(5-amino-1,2,4-thiadiazol-3-yl)-2-methoxyiminoacetamido]-3-[(2,3-cyclopenteno-4-carbamoyl-1-pyridinium)methyl]-3-cephem-4-carboxylate;

7-β-[(Z)-2-(2-aminothiazol-4-yl)-2-ethoxyiminoacetamido]-3-[(2,3-cyclopenteno-4-carbamoyl-1-pyridinium)methyl]-3-cephem-4-carboxylate;

7-β-[(Z)-2-(2-aminothiazol-4-yl)-2-(2-fluoroethoxyimino)acetamido]-3-[(2,3-cyclopenteno-4-carbamoyl-1-pyridinium)methyl]-3-cephem-4-carboxylate;

7-β-[(Z)-2-(2-aminothiazol-4-yl)-2-(2-propen-1-oxyimino)acetamido]-3-[(2,3-cyclopenteno-4-carbamoyl-1-pyridinium)methyl]-3-cephem-4-carboxylate;

7-β-[(Z)-2-(2-aminothiazol-4-yl)-2-methoxyiminoacetamido]-3-[(4-amino-2,3-cyclopenteno-1-pyridinium)methyl]-3-cephem-4-carboxylate;

7-β-[(Z)-2-(2-aminothiazol-4-yl)-2-methoxyiminoacetamido]-3-[(4-acetamido-2,3-cyclopenteno-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-methoxycarbonylamino-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-formamido-1-pyridinium)methyl]-3-cephem-4-carboxylate;

7-β-[(Z)-2-(2-aminothiazol-4-yl)-2-(carboxyprop-2-oxyimino)acetamido]-3-[(2,3-cyclopenteno-4-formamido-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-dimethylamino-1-pyridinium)methyl]-3-cephem-4-carboxylate;

7-β-[(Z)-2-(2-aminothiazol-4-yl)-2-hydroxyiminoacetamido]-3-[(2,3-cyclopenteno-4-formamido-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-cyano-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-(N-hydroxycarboxamidyl-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-(4-methylthiazol-2-yl)-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-(3-methyl-1,2,4-oxadiazol-5-yl)-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-(3-methyl-1,2,4-triazol-5-yl)-1-pyridinium)methyl]-3-cephem-4-carboxylate;

7-β-[(Z)-2-(2-aminothiazol-4-yl)-2-methoxyiminoacetamido]-3-[(2,3-cyclopenteno-4-(1,3,4-oxadiazol-2-yl)-1-pyridinium)methyl]-3-cephem-4-carboxylate; and 7-β-[(Z)-2-(2-aminothiazol-4-yl)-2-methoxyiminoacetamido]-3-[(2,3-cyclopenteno-4-(3-methyl-1,2,4-oxadiazol-3-yl)-1-pyridinium)methyl]-3-cephem-4-carboxylate.

3. The compound of claim 1 wherein said pharmacologically acceptable salt is a sulfate derivative of the compound.

4. A compound of formula (V):

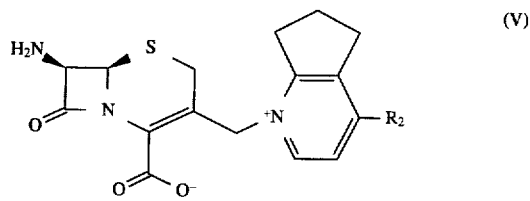

(V)

wherein $R_2$ has the same meaning as defined in claim 1.

5. A pharmaceutical composition comprising an effective amount of the compound or its derivative recited in claim 1 and a pharmacologically acceptable carrier.

* * * * *